US012180274B2

(12) United States Patent
Riedemann et al.

(10) Patent No.: US 12,180,274 B2
(45) Date of Patent: Dec. 31, 2024

(54) TREATMENT OF PNEUMONIA AND ARDS WITH INHIBITORS OF C5a AND IL-6 ACTIVITY

(71) Applicant: InflaRx GmbH, Jena (DE)

(72) Inventors: Niels Christoph Riedemann, Jena (DE); Renfeng Guo, Ann Arbor, MI (US)

(73) Assignee: InflaRx GmbH, Jena (DE)

( * ) Notice: Subject to any disclaimer, the term of this patent is extended or adjusted under 35 U.S.C. 154(b) by 0 days.

(21) Appl. No.: 18/324,915

(22) Filed: May 26, 2023

(65) Prior Publication Data

US 2024/0391995 A1 Nov. 28, 2024

(51) Int. Cl.
*C07K 16/24* (2006.01)
*A61P 11/00* (2006.01)

(52) U.S. Cl.
CPC ............ *C07K 16/248* (2013.01); *A61P 11/00* (2018.01); *C07K 16/24* (2013.01); *C07K 2317/565* (2013.01)

(58) Field of Classification Search
CPC ........ C07K 16/248; C07K 16/24; A61P 11/00
See application file for complete search history.

(56) References Cited

U.S. PATENT DOCUMENTS

| | | | |
|---|---|---|---|
| 4,704,355 A | 11/1987 | Bernstein | |
| 5,939,598 A | 8/1999 | Kucherlapati et al. | |
| 6,355,245 B1 | 3/2002 | Evans et al. | |
| 10,376,595 B2 | 8/2019 | Guo et al. | |
| 11,273,225 B2 | 3/2022 | Guo et al. | |
| 11,464,868 B2 | 10/2022 | Guo et al. | |
| 2003/0118592 A1 | 6/2003 | Ledbetter et al. | |
| 2003/0133939 A1 | 7/2003 | Ledbetter et al. | |
| 2004/0110226 A1 | 6/2004 | Lazar et al. | |
| 2010/0129346 A1 | 5/2010 | Mackay | |
| 2012/0219566 A1 | 8/2012 | Medof et al. | |
| 2012/0231008 A1 | 9/2012 | Guo et al. | |
| 2013/0004514 A1 | 1/2013 | Zahn et al. | |
| 2017/0137499 A1* | 5/2017 | Guo .................. A61P 31/12 |
| 2017/0349575 A1 | 12/2017 | Musicki et al. | |
| 2018/0280530 A1 | 10/2018 | Guo et al. | |
| 2018/0282425 A1 | 10/2018 | Guo et al. | |
| 2020/0061202 A1 | 2/2020 | Guo et al. | |
| 2020/0290969 A1 | 9/2020 | Li et al. | |
| 2021/0046191 A1 | 2/2021 | Guo et al. | |
| 2023/0158060 A1 | 5/2023 | Riedemann et al. | |
| 2023/0279087 A1 | 9/2023 | Guo et al. | |

FOREIGN PATENT DOCUMENTS

| | | |
|---|---|---|
| JP | 2012514465 A | 6/2012 |
| JP | 2014529997 A | 11/2014 |
| JP | 2015511965 A | 4/2015 |
| JP | 2016518331 A | 6/2016 |
| JP | 2016523829 A | 8/2016 |
| JP | 2017514791 A | 6/2017 |
| WO | 1991004014 A1 | 4/1991 |
| WO | 1999000406 A1 | 1/1999 |
| WO | 2001015731 A1 | 3/2001 |
| WO | 2003015819 A1 | 2/2003 |
| WO | 2003033528 A1 | 4/2003 |
| WO | 2005079363 A2 | 9/2005 |
| WO | 2005092366 A1 | 10/2005 |
| WO | 2006082406 A2 | 8/2006 |
| WO | 2008009062 A1 | 1/2008 |
| WO | 2008029167 A1 | 3/2008 |
| WO | 2010075257 A1 | 7/2010 |
| WO | 2010079314 A2 | 7/2010 |
| WO | 2011063980 A1 | 6/2011 |
| WO | 2011137395 A1 | 11/2011 |
| WO | 2011163640 A1 | 12/2011 |
| WO | 2013041730 A1 | 3/2013 |
| WO | 2013138586 A1 | 9/2013 |
| WO | 2014160129 A2 | 10/2014 |
| WO | 2014180961 A1 | 11/2014 |
| WO | 2015140304 A1 | 9/2015 |
| WO | 2016044419 A1 | 3/2016 |
| WO | 2016061066 A1 | 4/2016 |
| WO | 2016102877 A1 | 6/2016 |
| WO | 2016209956 A1 | 12/2016 |
| WO | 2017176620 A2 | 10/2017 |
| WO | 2017218515 A1 | 12/2017 |
| WO | 2018175833 A1 | 9/2018 |
| WO | 2018184739 A1 | 10/2018 |
| WO | 2018234118 A1 | 12/2018 |
| WO | 2020051418 A1 | 3/2020 |

(Continued)

OTHER PUBLICATIONS

Samaee et al. "Tocilizumab for treatment patients with COVID-19: Recommended medication for novel disease", Int Immunopharmacol. Dec. 2020; 89: 107018 (Year: 2020).*
Weiss et al. "Rapid mapping of protein functional epitopes by combinatorial alanine scanning", Proc Natl Acad Sci U S A. Aug. 1, 2000;97(16):8950-4. (Year: 2000).*
Yadav et al., "Is Acute Respiratory Distress Syndrome a Preventable Disease?", Am J Respir Crit Care Med. 2017 (Year: 2017).*
Carvelli et al., "Association of COVID-19 inflammation with activation of the C5a-C5aR1 axis," Nature, Dec. 2020, vol. 588, pp. 146-150.
Carvelli et al., "Identification of immune checkpoints in COVID-19," Research Square, 2020, pp. 1-30.
Czermak et al., "In Vitro and In Vivo Dependency of Chemokine Generation on C5a and TNF-α," The Journal of Immunology, 1999, vol. 162, pp. 2321-2325.

(Continued)

*Primary Examiner* — Amy E Juedes
*Assistant Examiner* — Peter Johansen
(74) *Attorney, Agent, or Firm* — Greenberg Traurig LLP; Melissa Hunter-Ensor; Leslie Serunian

(57) ABSTRACT

The present invention relates to an inhibitor of C5a activity and an inhibitor of IL-6 activity for use in the treatment of infectious pneumonia and infectious acute respiratory distress syndrome (ARDS). In further aspects administration regimes and kit of parts are referred to.

4 Claims, 3 Drawing Sheets

Figure 1:
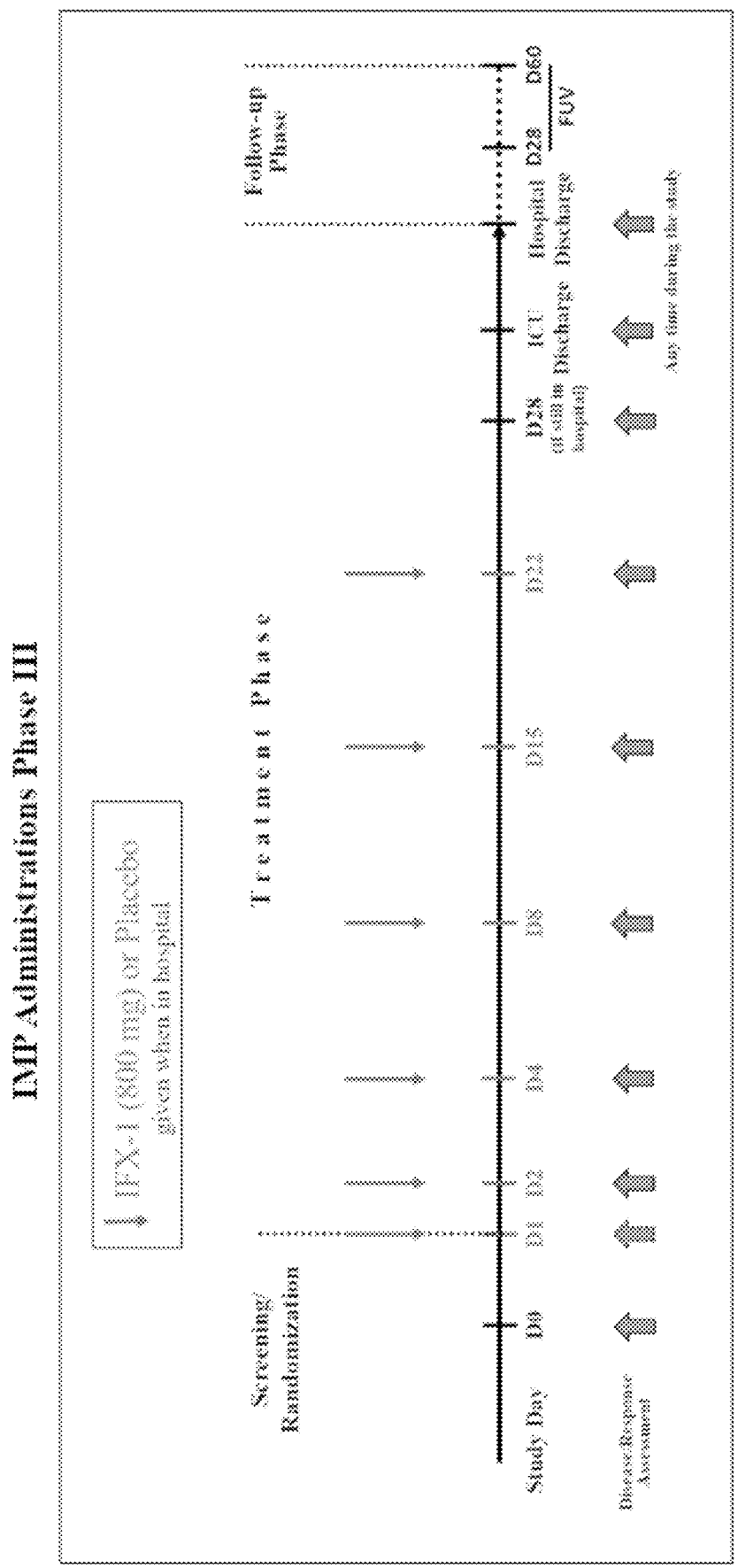

Specification includes a Sequence Listing.

(56) References Cited

FOREIGN PATENT DOCUMENTS

| WO | 2020182384 | A1 | | 9/2020 | |
|---|---|---|---|---|---|
| WO | 2020214716 | A1 | | 10/2020 | |
| WO | 2021188601 | A1 | | 9/2021 | |
| WO | WO-2021190770 | A1 | * | 9/2021 | ......... A61K 31/7125 |
| WO | WO-2021205013 | A1 | * | 10/2021 | |
| WO | WO-2021211940 | A1 | * | 10/2021 | ............. A61P 11/00 |

OTHER PUBLICATIONS

Gao et al., "Highly pathogenic coronavirus N protein aggravates lung injury by MASP-2-mediated complement over-activation," medRxiv, Mar. 2020, pp. 1-25.

Gralinski et al., "Complement Activation Contributes to Severe Acute Respiratory Syndrome Coronavirus Pathogenesis," mBio, 2018, vol. 9, No. 5, pp. e01753-18, pp. 1-15.

Guo et al., "Role of C5a in Inflammatory Responses," Annual Review of Immunology, 2005, vol. 23, pp. 821-852.

Höpken et al., "Inhibition of interleukin-6 synthesis in an animal model of septic shock by anti-C5a monoclonal antibodies," European Journal of Immunology, 1996, vol. 26, pp. 1103-1109.

Huber-Lang et al., "Role of C5a in Multiorgan Failure During Sepsis," The Journal of Immunology, 2001, vol. 166, pp. 1193-1199.

Jiang et al., "Blockade of the C5a-C5aR axis alleviates lung damage in hDPP4-transgenic mice infected with MERS-CoV," Emerging Microbes & Infections, 2018, vol. 7, Article No. 77, pp. 1-12.

RCSB Protein 4UU9: Crystal structure of the human c5a in complex with MEDI7814 a neutralising antibody; retrieved from the Internet on May 26, 2023.

Riedemann et al., "Expression and Function of the C5a Receptor in Rat Alveolar Epithelial Cells," The Journal of Immunology, 2002, vol. 168, pp. 1919-1925.

Riedemann et al., "Regulatory Role of C5a on Macrophage Migration Inhibitory Factor Release from Neutrophils," The Journal of Immunology, 2004, vol. 173, pp. 1355-1359.

Rittirsch et al., "Harmful molecular mechanisms in sepsis," Nature Reviews Immunology, Oct. 2008, vol. 8, pp. 776-787.

Strieter et al., "Cytokine-induced Neutrophil-derived Interleukin-8," American Journal of Pathology, Aug. 1992, vol. 141, No. 2, pp. 397-407.

Sun et al., "Treatment With Anti-C5a Antibody Improves the Outcome of H7N9 Virus Infection in African Green Monkeys," Clinical Infectious Diseases, 2015, vol. 60, No. 4, pp. 586-595.

UniProtKB P01031: CO5_Human; retrieved from the Internet on May 26, 2023 (13 pages).

UniProtKB P05231: IL6_Human; retrieved from the Internet on May 26, 2023 (12 pages).

Vlaar et al., "Anti-C5a antibody IFX-1 (vilobelimab) treatment versus best supportive care for patients with severe COVID-19 (PANAMO): an exploratory, open-label, phase 2 randomised controlled trial," The Lancet Rheumatology, Dec. 2020, vol. 2, pp. e764-e773.

Wang et al., "Clinical Characteristics of 138 Hospitalized Patients With 2019 Novel Coronavirus-Infected Pneumonia In Wuhan, China," JAMA, Mar. 17, 2020, vol. 323, No. 11, pp. 1061-1069.

Ward, Peter A., "Functions of C5a receptors," Journal of Molecular Medicine, Apr. 2009, vol. 87, pp. 375-378.

Zhou et al., "Clinical course and risk factors for mortality of adult inpatients with COVID-19 in Wuhan, China: a retrospective cohort study," The Lancet, Mar. 28, 2020, vol. 395, pp. 1054-1062.

Guo et al., "Divergent Signaling Pathways in Phagocytic Cells during Sepsis," The Journal of Immunology, 2006, vol. 177, No. 2, pp. 1306-1313.

Guo et al., "IFX-1 blocking the anaphylatoxin C5a—an anti-inflammatory effect in patients with hidradenitis suppurativa," Aug. 29, 2017, poster (1 page).

Harding, J., "Eculizumab," Drugs of the Future, 2004, vol. 29, No. 7, pp. 673-676.

Heap et al., "Analysis of a 17-amino acid residue, virus-neutralizing microantibody," Journal of General Virology, 2005, vol. 86, pp. 1791-1800.

Holliger et al., "'Diabodies': Small bivalent and bispecific antibody fragments," Proceedings of the National Academy of Sciences of the United States of America, Jul. 1993, vol. 90, No. 14, pp. 6444-6448.

Howard III et al., "Intracerebral drug delivery in rats with lesion-induced memory deficits," Journal of Neurosurgery, Jul. 1989, vol. 71, pp. 105-112.

Huang et al., "Clinical features of patients infected with 2019 novel coronavirus in Wuhan, China," The Lancet, Feb. 15, 2020, vol. 395, pp. 497-506.

Huber-Lang et al., "Complement-Induced Impairment of Innate Immunity During Sepsis," The Journal of Immunology, 2002, vol. 169, No. 6, pp. 3223-3231.

Huber-Lang et al., "Protective effects of anti-C5a peptide antibodies in experimental sepsis," The FASEB Journal, Jan. 19, 2001, vol. 15, No. 3, pp. 568-570.

Huston et al., "Protein engineering of antibody binding sites: Recovery of specific activity in an anti-digoxin single-chain Fv analogue produced in *Escherichia coli*," Proceedings of the National Academy of Sciences of the United States of America, Aug. 1988, vol. 85, pp. 5879-5883.

Hycult Biotech Catalog, "Complement and Collectins," 2020-2021, Uden, The Netherlands, pp. 1-8.

Hyzewicz et al., "Low-Intensity Training and the C5a Complement Antagonist NOX-D21 Rescue the mdx Phenotype through Modulation of Inflammation," The American Journal of Pathology, May 2017, vol. 187, No. 5, pp. 1147-1161.

Imagawa et al., "Consequences of cell membrane attack by complement: Release of arachidonate and formation of inflammatory derivatives," Proceedings of the National Academy of Sciences of the United States of America, Nov. 1983, vol. 80, pp. 6647-6651.

Inflarx, "InflaRx initiates exploratory Phase II trial with IFX-1, a first-in-class anti-complement C5a antibody, in patients with Hidradenitis Suppurativa," Jan. 4, 2017, pp. 1-2.

Inflarx, "InflaRx Reports Additional Analysis of the SHINE Phase IIb Results for IFX-1 in Hidradenitis Suppurativa," Jul. 18, 2019, pp. 1-9.

Inflarx "InflaRx Reports Positive Results from the Open Label Extension Part of the Shine Study for IFX-1 in Hidradenitis Suppurativa," Nov. 6, 2019, pp. 1-8.

Ip et al., "Mannose-Binding Lectin in Severe Acute Respiratory Syndrome Coronavirus Infection," The Journal of Infectious Diseases, May 15, 2005, vol. 191, pp. 1697-1704.

Jayne et al., "Randomized Trial of C5a Receptor Inhibitor Avacopan in ANCA-Associated Vasculitis," Journal of the American Society of Nephrology, 2017, vol. 28, pp. 2756-2767.

Jemec, "Medical treatment of hidradenitis suppurativa," Expert Opinion on Pharmacotherapy, 2004, vol. 5, No. 8, pp. 1767-1770.

Jemec et al., "The prevalence of hidradenitis suppurativa and its potential precursor lesions," Journal of the American Academy of Dermatology, Aug. 1996, vol. 35, No. 2, Pt. 1, pp. 191-194.

Jorizzo et al., "Low-dose weekly methotrexate for unusual neutrophilic vascular reactions: Cutaneous polyarteritis nodosa and Behcet's disease," Journal of the American Academy of Dermatology, Jun. 1991, vol. 24, No. 6, Pt. 1, pp. 973-978.

Kaplan, M., "Eculizumab," Current Opinion in Investigational Drugs, 2002, vol. 3, No. 7, pp. 1017-1023.

Kaplan, Mariana J., "Role of neutrophils in systemic autoimmune diseases," Arthritis Research & Therapy, 2013, vol. 15, Article No. 219, pp. 1-9.

Keseroglu et al., "A Case of Subcorneal Pustular Dermatosis Successfully Treated with Acitretin," Archives of Inflammation, Oct. 27, 2016, vol. 1, No. 2, pp. 1-3.

Khameneh et al., "C5a Regulates IL-1B Production and Leukocyte Recruitment in a Murine Model of Monosodium Urate Crystal-Induced Peritonitis," Frontiers in Pharmacology, Jan. 23, 2017, vol. 8, Article 10, pp. 1-11.

Kimball et al., "Assessing the validity, responsiveness and meaningfulness of the Hidradenitis Suppurativa Clinical Response (HiSCR)

(56) References Cited

OTHER PUBLICATIONS as the clinical endpoint for hidradenitis suppurativa treatment," British Journal of Dermatology, 2014, vol. 171, No. 6, pp. 1434-1442.

Klos et al., "International Union of Basic and Clinical Pharmacology. [corrected]. LXXXVII. Complement Peptide C5a, C4a, and C3a Receptors," Pharmacological Reviews, Jan. 2013, vol. 65, pp. 500-543.

Klos et al., "The role of the anaphylatoxins in health and disease," Molecular Immunology, 2009, vol. 46, pp. 2753-2766.

Kurzen et al., "What causes hidradenitis suppurativa?" Experimental Dermatology, 2008, vol. 17, No. 5, pp. 455-456.

Kussie et al., "A Single Engineered Amino Acid Substitution Changes Antibody Fine Specificity," Journal of Immunology, 1994, vol. 152, pp. 146-152.

Langer et al., "Chemical and Physical Structure of Polymers as Carriers for Controlled Release of Bioactive Agents: A Review," Journal of Macromolecular Science, Reviews in Macromolecular Chemistry and Physics, 1983, vol. 23, No. 1, pp. 61-126.

Langer, Robert, "New Methods of Drug Delivery," Science, Sep. 28, 1990, vol. 249, pp. 1527-1533.

Lee et al., "A Major Outbreak of Severe Acute Respiratory Syndrome in Hong Kong," The New England Journal of Medicine, May 15, 2003, vol. 348, No. 20, pp. 1986-1994.

Levy et al., "Inhibition of Calcification of Bioprosthetic Heart Valves by Local Controlled-Release Diphosphonate," Science, Apr. 12, 1985, vol. 228, pp. 190-192.

Li et al., "Metformin reduces diabetes-related inflammatory molecules in human vitreous and retinal vascular endothelial cells," Investigative Ophthalmology & Visual Science, Sep. 2016, vol. 57, p. 6346; abstract submitted for the 2016 Annual Meeting of the Association for Research in Vision and Opthamology (ARVO).

Li et al., "Neuroprotective effects of argatroban and C5a receptor antagonist (PMX53) following intracerebral haemorrhage," Clinical and Experimental Immunology, 2014, vol. 175, No. 2, pp. 285-295.

Lima et al., "Keratinocytes and neutrophils are important sources of proinflammatory molecules in hidradenitis suppurativa," British Journal of Dermatology, 2016, vol. 174, pp. 514-521.

Liu et al., "Neutrophil-to-Lymphocyte Ratio Predicts Severe Illness Patients with 2019 Novel Coronavirus in the Early Stage," medRxiv, Feb. 12, 2020, pp. 1-14.

Liu et al., "Study on interaction between SARS-CoV N and MAP19," Chinese Journal of Cellular and Molecular Immunology, 2009, vol. 25, No. 9, pp. 777-779. [English Abstract].

Ma et al., "Incidence, clinical characteristics and prognostic factor of patients with COVID-19: a systematic review and meta-analysis," medRxiv, Mar. 20, 2020, pp. 1-51.

March et al., "Potent Cyclic Antagonists of the Complement C5a Receptor on Human Polymorphonuclear Leukocytes. Relationships between Structures and Activity," Molecular Pharmacology, 2004, vol. 65, No. 4, pp. 868-879.

Markiewski et al., "Modulation of the anti-tumor immune response by complement," Nature Immunology, Nov. 2008, vol. 9, No. 11, pp. 1225-1235.

Marzano et al., "Association of Pyoderma Gangrenosum, Acne, and Suppurative Hidradenitis (PASH) Shares Genetic and Cytokine Profiles With Other Autoinflammatory Diseases," Medicine, Dec. 2014, vol. 93, No. 27, e187, pp. 1-11.

Marzano et al., "Hidradenitis suppurativa, neutrophilic dermatoses and autoinflammation: what's the link?" British Journal of Dermatology, 2016, vol. 174, pp. 482-483.

Merle et al., "Complement System Part I—Molecular Mechanisms of Activation and Regulation," Frontiers in Immunology, Jun. 2, 2015, vol. 6, Article 262, pp. 1-30.

Morgan et al., "Complement, a target for therapy in inflammatory and degenerative diseases," Nature Reviews Drug Discovery, Dec. 2015, vol. 14, pp. 857-877.

Navarini et al., "Neutrophilic dermatoses and autoinflammatory diseases with skin involvement-innate immune disorders," Seminars in Immopathology, 2016, vol. 38, pp. 45-56.

Németh et al., "Neutrophils in animal models of autoimmune disease," Seminars in Immunology, Apr. 2016, vol. 28, No. 2, pp. 174-186.

Nunez-Cruz et al., "Genetic and Pharmacologic Inhibition of Complement Impairs Endothelial Cell Function and Ablates Ovarian Cancer Neovascularization," Neoplasia, Nov. 2012, vol. 14, No. 11, pp. 994-1004.

Okroj et al., "Functional Analyses of Complement Convertases Using C3 and C5-Depleted Sera," PLoS One, Oct. 2012, vol. 7, No. 10, e47245, pp. 1-13.

Allegretti et al., "Targeting C5a: Recent Advances in Drug Discovery," Current Medicinal Chemistry, 2005, vol. 12, No. 2, pp. 217-236.

Almagro et al., "Humanization of antibodies," Frontiers in Bioscience, Jan. 1, 2008, vol. 13, pp. 1619-1633.

Ami et al., "Co-infection of respiratory bacterium with severe acute respiratory syndrome coronavirus induces an exacerbated pneumonia in mice," Microbiology and Immunology, 2008, vol. 52, pp. 118-127.

Anonymous, "No significant treatment effect found for IFX-1 in hidradenitis suppurativa trial," Jun. 7, 2019, retrieved from the Internet on Nov. 12, 2019, <https://www.healio.com/dermatology/skin-care/news/online/{72df4fe7-aaec-41b0-be1f-0179ed471924}/no-significant-treatment-effect-found-for-ifx-1-in-hidradenitis-suppurativa-trial> (2 pages).

Argyropoulou et al., "An Open-Label Trial to Assess the Safety of IFX-1 in Patients with Hidradenitis Suppurativa Not Eligible for Adalimumab," Aug. 4, 2017, poster (1 page).

Bekker et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," PLoS One, Oct. 21, 2016, vol. 11, No. 10, e0164646, pp. 1-19.

Beinrohr et al., "C1, MBL-MASPs and C1-inhibitor: novel approaches for targeting complement-mediated inflammation," Trends in Molecular Medicine, 2008, vol. 14, No. 12, pp. 511-521.

Biedermann et al., "Regulation of T cell immunity in atopic dermatitis by microbes: the Yin and Yang of cutaneous inflammation," Frontiers in Immunology, Jul. 13, 2015, vol. 6, Article 353, pp. 1-9.

Binz et al., "Engineering novel binding proteins from nonimmunoglobulin domains," Nature Biotechnology, Oct. 2005, vol. 23, No. 10, pp. 1257-1268.

Bird et al., "Single-Chain Antigen-Binding Proteins," Science, Oct. 21, 1988, vol. 242, pp. 423-426.

Blok et al., "Gene expression profiling of skin and blood in hidradenitis suppurativa," British Journal of Dermatology, 2016, vol. 174, pp. 1392-1394.

Braun-Falco et al., "Pyoderma gangrenosum, acne, and suppurative hidradenitis (PASH)—a new autoinflammatory syndrome distinct from PAPA syndrome," Journal of the American Academy of Dermatology, Mar. 2012, vol. 66, No. 3, pp. 409-415.

Brody et al., "Aptamers as therapeutic and diagnostic agents," Reviews in Molecular Biotechnology, 2000, vol. 74, pp. 5-13.

Buchwald et al., "Long-term, continuous intravenous heparin administration by an implantable infusion pump in ambulatory patients with recurrent venous thrombosis," Surgery, Oct. 1980, vol. 88, No. 4, pp. 507-516.

Cannon, "Analog Design," Chapter 19 in Burger's Medicinal Chemistry and Drug Discovery, 5th Edition, vol. I: Principles and Practice, 1995, pp. 783-802.

Chan et al., "Middle East Respiratory Syndrome Coronavirus: Another Zoonotic Betacoronavirus Causing SARS-Like Disease," Clinical Microbiology Reviews, Apr. 2015, vol. 28, No. 2, pp. 465-522.

Chang et al., "Epidemiologic and Clinical Characteristics of Novel Coronavirus Infections Involving 13 Patients Outside Wuhan, China," JAMA, Mar. 17, 2020, vol. 323, No. 11, pp. 1092-1093.

Che et al., "Nucleocapsid Protein as Early Diagnostic Marker for SARS," Emerging Infectious Diseases, Nov. 2004, vol. 10, No. 11, pp. 1947-1949.

(56) References Cited

OTHER PUBLICATIONS

Chen et al., "Clinical and immunologic features in severe and moderate forms of Coronavirus Disease 2019," medRxiv, Feb. 19, 2020, pp. 1-33.
Chen et al., "Enhancement and destruction of antibody function by somatic mutation: unequal occurrence is controlled by V gene combinatorial associations," The EMBO Journal, 1995, vol. 14, No. 12, pp. 2784-2794.
Chen et al., "Epidemiological and clinical characteristics of 99 cases of 2019 novel coronavirus pneumonia in Wuhan, China: a descriptive study," The Lancet, Feb. 15, 2020, vol. 395, pp. 507-513.
Chen et al., "Plasma proteome of severe acute respiratory syndrome analyzed by two-dimensional gel electrophoresis and mass spectrometry," Proceedings of the National Academy of Sciences of the United States of America, Dec. 7, 2004, vol. 101, No. 49, pp. 17039-17044.
ClinicalTrials.gov archive, "History of Changes for Study: NCT03001622, Studying Complement Inhibition in Patients With Moderate to Severe Hidradenitis Suppurativa," Study NCT03001622, Submitted Date: Dec. 20, 2016 (v1), pp. 1-5.
ClinicalTrials.gov archive, "History of Changes for Study: NCT03001622, Studying Complement Inhibition in Patients With Moderate to Severe Hidradenitis Suppurativa," Study NCT03001622, Submitted Date: Mar. 20, 2017 (v3), pp. 1-6.
Colman, P. M., "Effects of amino acid sequence changes on antibody-antigen interactions," Research in Immunology, Jan. 1994, vol. 145, No. 1, pp. 33-36.
Cugno et al., "PAPA, PASH and PAPASH Syndromes: Pathophysiology, Presentation and Treatment," American Journal of Clinical Dermatology, Feb. 2017, vol. 18, pp. 555-562.
Cole et al., "Beyond lysis: how complement influences cell fate," Clinical Science, 2003, vol. 104, pp. 455-466.
Cumpelik et al., "Neutrophil microvesicles resolve gout by inhibiting C5a-mediated priming of the inflammasome," Annals of the Rheumatic Diseases, 2016, vol. 75, No. 6, pp. 1236-1245.
Czermak et al., "Protective effects of C5a blockade in sepsis," Nature Medicine, Jul. 1999, vol. 5, No. 7, pp. 788-792.
D'Angelo et al., "Many Routes to an Antibody Heavy-Chain CDR3: Necessary, Yet Insufficient, for Specific Binding," Frontiers in Immunology, Mar. 2018, vol. 9, Article 395, pp. 1-13.
Dang et al., "Role of the complement anaphylatoxin C5a-receptor pathway in atopic dermatitis in mice," Molecular Medicine Reports, 2015, vol. 11, pp. 4183-4189.
Deming et al., "Vaccine Efficacy in Senescent Mice Challenged with Recombinant SARS-CoV Bearing Epidemic and Zoonotic Spike Variants," PLoS Medicine, Dec. 2006, vol. 3, No. 12, e525, pp. 2359-2375.
Devyatyarova-Johnson et al., "The Lipopolysaccharide Structures of *Salmonella enterica* Serovar Typhimurium and Neisseria gonorrhoeaeDetermine the Attachment of Human Mannose-Binding Lectin to Intact Organisms," Infection and Immunity, Jul. 2000, vol. 68, No. 7, pp. 3894-3899.
Dhingra et al., "Attenuated neutrophil axis in atopic dermatitis compared to psoriasis reflects TH17 pathway differences between these diseases," Journal of Allergy and Clinical Immunology, Aug. 2013, vol. 132, No. 2, pp. 1-7.
Drosten et al., "Identification of a Novel Coronavirus in Patients with Severe Acute Respiratory Syndrome," The New England Journal of Medicine, May 15, 2003, vol. 348, No. 20, pp. 1967-1976.
Dunkelberger et al., "Complement and its role in innate and adaptive immune responses," Cell Research, 2010, vol. 20, pp. 34-50.
During et al., "Controlled Release of Dopamine from a Polymeric Brain Implant: In Vivo Characterization," Annals of Neurology, Apr. 1989, vol. 25, No. 4, pp. 351-356.
Fan et al., "Clinical Features of COVID-19-Related Liver Damage," medRxiv, Feb. 28, 2020, pp. 1-21.
Finch et al., "Low-Molecular-Weight Peptidic and Cyclic Antagonists of the Receptor for the Complement Factor C5a," Journal of Medicinal Chemistry, 1999, vol. 42, No. 11, pp. 1965-1974.
Gál et al., "A True Autoactivating Enzyme: Structural Insight into Mannose-Binding Lectin-Associated Serine Protease-2 Activations," The Journal of Biological Chemistry, Sep. 30, 2005, vol. 280, No. 39, pp. 33435-33444.
Gao et al., "Expression in *Escherichia coli* and Purification of Full Length Recombinant Human MASP2," Letters in Biotechnology, Nov. 2011, vol. 22, No. 6, pp. 806-808 and 891. [English Abstract].
Garcia et al., "Complement C5 Activation during Influenza A Infection in Mice Contributes to Neutrophil Recruitment and Lung Injury," PLoS One, May 2013, vol. 8, No. 5, e64443, pp. 1-11.
Giamarellos-Bourboulis et al., "Abstract: OO3-2 | Complement activation in hidradenitis suppurativa," Experimental Dermatology, 2017, vol. 26, Suppl. 1, pp. 3-38.
Goodson, J. Max, "Dental Applications," Medical Applications of Controlled Release, 1984, vol. II, Chapter 6, pp. 115-138.
Graham et al., "A decade after SARS: strategies for controlling emerging coronaviruses," Nature Reviews Microbiology, Dec. 2013, vol. 11, pp. 836-848.
Graille et al., "CA206: PAPA, PASH, PAPASH, PsAPASH, PASS . . . des syndromes auto-inflammatoires PAS si simples," La Revue de Médecine Interne, 2015, vol. 36, pp. A205-A206.
Gralinski et al., "Complement Activation Contributes to Severe Acute Respiratory Syndrome Coronavirus Pathogenesis," mBio, Sep./Oct. 2018, vol. 9, No. 5, e01753-18, pp. 1-15.
Gueler et al., "Complement 5a Receptor Inhibition Improves Renal Allograft Survival," Journal of the American Society of Nephrology, 2008, vol. 19, pp. 2302-2312.
Oppermann et al., "Probing the Human Receptor for C5a Anaphylatoxin with Site-Directed Antibodies: Identification of a Potential Ligand Binding Site on the NH2-Terminal Domain," The Journal of Immunology, Oct. 1993, vol. 151, No. 7, pp. 3785-3794.
Pang et al., "Serum Proteomic Fingerprints of Adult Patients with Severe Acute Respiratory Syndrome," Clinical Chemistry, 2006, vol. 52, No. 3, pp. 421-429.
Pawaria et al., "Complement Component C5a Permits the Coexistence of Pathogenic Th17 Cells and Type 1 IFN in Lupus," The Journal of Immunology, 2014, vol. 193, No. 7, pp. 3288-3295.
Petersen et al., "An assay for the mannan-binding lectin pathway of complement activation," Journal of Immunological Methods, 2001, vol. 257, pp. 107-116.
Petitclerc et al., "Pathologic Leukocyte Infiltration of the Rabbit Aorta Confers a Vasomotor Effect to Chemotactic Peptides Through Cyclooxygenase-Derived Metabolites," The Journal of Immunology, May 1996, vol. 156, No. 9, pp. 3426-3434.
Piche-Nicholas et al., "Changes in complementarity-determining regions significantly alter IgG binding to the neonatal Fc receptor (FcRn) and pharmacokinetics," MABS, 2018, vol. 10, No. 1, pp. 81-94.
Prat et al., "Neutrophilic dermatoses as systemic diseases," Clinics in Dermatology, 2014, vol. 32, No. 3, pp. 376-388.
Proctor et al., "Transdermal Pharmacology of Small Molecule Cyclic C5a Antagonists," Advances in Experimental Medicine and Biology, 2006, vol. 586, pp. 329-345.
Qiu et al., "Small antibody mimetics comprising two complementarity-determining regions and a framework region for tumor targeting," Nature Biotechnology, 2007, vol. 25, No. 8, pp. 921-929.
Rawal et al., "Activation of Complement Component C5: Comparison of C5 Convertases of the Lectin Pathway and the Classical Pathway of Complement," The Journal of Biological Chemistry, Mar. 21, 2008, vol. 283, No. 12, pp. 7853-7863.
Ren et al., "The use of proteomics in the discovery of serum biomarkers from patients with severe acute respiratory syndrome," Proteomics, 2004, vol. 4, No. 11, pp. 3477-3484.
Revuz J., "Hidradenitis suppurativa," Journal of the European Academy of Dermatology and Venereology, 2009, vol. 23, No. 9, pp. 985-998.
Ricardo et al., "Preclinical Evaluation of RA101495, a Potent Cyclic Peptide Inhibitor of C5 for the Treatment of Paroxysmal Nocturnal Hemoglobinuria," Blood, 2015, vol. 126, No. 23, p. 939.

(56) References Cited

OTHER PUBLICATIONS

Ricklin et al., "The renaissance of complement therapeutics," Nature Reviews: Nephrology, Jan. 2018, vol. 14, pp. 26-47.
Riedemann et al., "Controlling the anaphylatoxin C5a in diseases requires a specifically targeted inhibition," Clinical Immunology, 2017, vol. 180, pp. 25-32.
Riedemann et al., "Increased C5a receptor expression in sepsis," The Journal of Clinical Investigation, Jul. 2002, vol. 110, No. 1, pp. 101-108.
Rittirsch et al., "Functional roles for C5a receptors in sepsis," Nature Medicine, May 2008, vol. 14, No. 5, pp. 551-557.
Rota et al., "Characterization of a Novel Coronavirus Associated with Severe Acute Respiratory Syndrome," Science, May 30, 2003, vol. 300, pp. 1394-1399.
Rudikoff et al., "Single amino acid substitution altering antigen-binding specificity," Proceedings of the National Academy of Sciences of the United States of America, Mar. 1982, vol. 79, pp. 1979-1983.
Sánchez-Galán et al., "Leukotriene B4 enhances the activity of nuclear factor-kB pathway through BLT1 and BLT2 receptors in atherosclerosis," Cardiovascular Research, 2009, vol. 81, pp. 216-225.
Sarma et al., "Complement in lung disease," Autoimmunity, Aug. 2006, vol. 39, No. 5, pp. 387-394.
Saudek et al., "A Preliminary Trial of the Programmable Implantable Medication System for Insulin Delivery," The New England Journal of Medicine, Aug. 31, 1989, vol. 321, No. 9, pp. 574-579.
Schatz-Jakobsen et al., "Structural and functional characterization of human and murine C5a anaphylatoxins," Acta Crystallographica Section D Biological Crystallography, Jun. 2014, vol. 70, Pt. 6, pp. 1704-1717.
Schwaeble et al., "Targeting of mannan-binding lectin-associated serine protease-2 confers protection from myocardial and gastrointestinal ischemia/reperfusion injury," Proceedings of the National Academy of Sciences of the United States of America, May 3, 2011, vol. 108, No. 18, pp. 7523-7528.
Sefton, Michael V., "Implantable Pumps," CRC Critical Reviews in Biomedical Engineering, 1987, vol. 14, No. 3, pp. 201-240.
Slade et al., "Hidradenitis suppurativa: pathogenesis and management," British Journal of Plastic Surgery, 2003, vol. 56, No. 5, pp. 451-461.
Smith, Kristen, "If at first you don't succeed . . . ," Jul. 2019; retrieved from the Internet on Nov. 12, 2019 <https://www.ddn-news.com/index.php?newsarticle=13478> (2 pages).
Song et al., "C5a receptor1 inhibition alleviates influenza virus-induced acute lung injury," International Immunopharmacology, 2018, vol. 59, pp. 12-20.
Souza et al., "APT070 (Mirococept), a membrane-localised complement inhibitor, inhibits inflammatory responses that follow intestinal ischaemia and reperfusion injury," British Journal of Pharmacology, 2005, vol. 145, No. 8, pp. 1027-1034.
Strainic et al., "Absent C3a and C5a receptor signaling into CD4+ T cells enables auto-inductive TGF-β1 signaling and induction of Foxp3+ T regulatory cells," Nature Immunology, Feb. 2013, vol. 14, No. 2, pp. 162-171.
Sun et al., "Inhibition of Complement Activation Alleviates Acute Lung Injury Induced by Highly Pathogenic Avian Influenza H5N1 Virus Infection," American Journal of Respiratory Cell and Molecular Biology, Aug. 2013, vol. 49, No. 2, pp. 221-230.
Surjit et al., "The Severe Acute Respiratory Syndrome Coronavirus Nucleocapsid Protein Is Phosphorylated and Localizes in the Cytoplasm by 14-3-3-Mediated Translocation," Journal of Virology, Sep. 2005, vol. 79, No. 17, pp. 11476-11486.
Tagami, "Recent topics in sterile pustular dermatoses," Japanese Journal of Inflammation, 1986, vol. 6, No. 1, pp. 5-14.
Takahashi et al., "The mannose-binding lectin: a prototypic pattern recognition molecule," Current Opinion in Immunology, 2006, vol. 18, pp. 16-23.
Tang et al., "Abnormal coagulation parameters are associated with poor prognosis in patients with novel coronavirus pneumonia," Journal of Thrombosis and Haemostasis, 2020, vol. 18, pp. 844-847.
Tang et al., "Anticoagulant treatment is associated with decreased mortality in severe coronavirus disease 2019 patients with coagulopathy," Journal of Thrombosis and Haemostasis, 2020, vol. 18, pp. 1094-1099.
Taylor, Phil, "InflaRx flatlines after skin disease drug flops in midstage trial," pharmaphorum, Jun. 6, 2019; retrieved from the Internet on Nov. 12, 2019 <https://pharmaphorum.com/news/inflarx-flatlines-skin-disease-drug-midstage-trial/> (2 pages).
Ternowitz et al., "Methotrexate Inhibits the Human C5a-Induced Skin Response in Patients with Psoriasis," The Journal of Investigative Dermatology, Aug. 1987, vol. 89, No. 2, pp. 192-196.
Tesar et al., "Avacopan in the treatment of ANCA-associated vasculitis," Expert Opinion on Investigational Drugs, 2018, vol. 27, No. 5, pp. 491-496.
Treat et al., "Liposome Encapsulated Doxorubicin Preliminary Results of Phase I and Phase II Trials," Liposomes in the Therapy of Infectious Diseases and Cancer, Lopez-Berestein and Fidler (eds.), 1989, pp. 353-365.
Tzanetakou et al., "Safety and Efficacy of Anakinra in Severe Hidradenitis Suppurativa: A Randomized Clinical Trial," JAMA Dermatology, 2016, vol. 152, No. 1, pp. 52-59.
USBiological Life Sciences Certificate of Analysis for Antibody Clone No. 7H110 (Mouse Anti-Human CD88 Antibody), Date of Manufacture: May 17, 2017 (1 page).
Verdolini et al., "Metformin for the treatment of hidradenitis suppurativa: a little help along the way," Journal of the European Academy of Dermatology and Venereology, 2013, vol. 27, No. 9, pp. 1101-1108.
Wallis, Russell, "Interactions between mannose-binding lectin and MASPs during complement activation by the ectin pathway," Immunobiology, 2007, vol. 212, pp. 289-299.
Wang et al., "Consecutive false-negative rRT-PCR test results for SARS-CoV-2 in patients after clinical recovery from COVID-19," Journal of Medical Virology, 2020, vol. 92, pp. 2887-2890.
Wang et al., "The role of C5a in acute lung injury induced by highly pathogenic viral infections," Emerging Microbes & Infections, 2015, vol. 4, e28, pp. 1-7.
Ward et al., "Binding activities of a repertoire of single immunoglobulin variable domains secreted from *Escherichia coli*," Nature, Oct. 12, 1989, vol. 341, pp. 544-546.
Werfel et al., "C5a receptors are detectable on mast cells in normal human skin and in psoriatic plaques but not in weal and flare reactions or in urticaria pigmentosa by immunohistochemistry," Archives of Dermatological Research, 1997, vol. 289, pp. 83-86.
Wills-Karp, Marsha, "Complement Activation Pathways: A Bridge between Innate and Adaptive Immune Responses in Asthma," Proceedings of the American Thoracic Society, 2007, vol. 4, pp. 247-251.
Wollina et al., "Acne inversa (*Hidradenitis suppurativa*): A review with a focus on pathogenesis and treatment," Indian Dermatology Online Journal, Jan.-Mar. 2013, vol. 4, No. 1, pp. 2-11.
World Health Organization Multicentre Collaborative Network for Severe Acute Respiratory Syndrome (SARS) Diagnosis, "A multicentre collaboration to investigate the cause of severe acute respiratory syndrome," The Lancet, May 17, 2003, vol. 361, pp. 1730-1733.
Xu et al., "Complement C5a regulates IL-17 by affecting the crosstalk between DC and γδ T cells in CLP-induced sepsis," European Journal of Immunology, 2010, vol. 40, No. 4, pp. 1079-1088.
Yasui et al., "Prior Immunization with Severe Acute Respiratory Syndrome (SARS)-Associated Coronavirus (SARS-CoV) Nucleocapsid Protein Causes Severe Pneumonia in Mice Infected with SARS-CoV," The Journal of Immunology, 2008, vol. 181, pp. 6337-6348.
Yu et al., "Measures for diagnosing and treating infections by a novel coronavirus responsible for a pneumonia outbreak originating in Wuhan, China," Microbes and Infection, 2020, vol. 22, pp. 74-79.
Zhang et al., "Antibody Responses Against SARS Coronavirus Are Correlated With Disease Outcome of Infected Individuals," Journal of Medical Virology, 2006, vol. 78, pp. 1-8.

(56) References Cited

OTHER PUBLICATIONS

Zhang et al., "Clinical characteristics of 82 death cases with COVID-19," medRxiv, Feb. 27, 2020, pp. 1-30.
Zhou et al., "A Single Asparagine-Linked Glycosylation Site of the Severe Acute Respiratory Syndrome Coronavirus Spike Glycoprotein Facilitates Inhibition by Mannose-Binding Lectin through Multiple Mechanisms," Journal of Virology, Sep. 2010, vol. 84, No. 17, pp. 8753-8764.
Zhou et al., "Active Replication of Middle East Respiratory Syndrome Coronavirus and Aberrant Induction of Inflammatory Cytokines and Chemokines in Human Macrophages: Implications for Pathogenesis," The Journal of Infectious Diseases, May 2014, vol. 209, pp. 1331-1342.
Zhou et al., "A pneumonia outbreak associated with a new coronavirus of probable bat origin," Nature, Mar. 12, 2020, vol. 579, pp. 270-273.
Annane et al., "Intravenous ravulizumab in mechanically ventilated patients hospitalised with severe COVID-19: a phase 3, multicentre, open-label, randomised controlled trial," The Lancet: Respiratory Medicine, Dec. 2023, vol. 11, No. 12, pp. 1051-1063.
Anonymous, "Emergency Use Authorization (EUA) for Vilobelimab (IFX-1) Center for Drug Evaluation and Research (CDER) Review," Feb. 1, 2023, 105 pages, Retrieved from the Internet on Dec. 5, 2023; URL: <https://www.gohibic.com/>.
Mourvillier et al., "LB1529. Randomized, Controlled Phase 3 Study of anti-C5a Vilobelimab's Effect on Mortality in Critically Ill COVID-19 Patients: A Therapy for Viral Pneumonia," Open Forum Infectious Diseases, Dec. 2022, vol. 9, Suppl. 2, p. S925.
International Search Report and Written Opinion mailed Jan. 5, 2024 in corresponding International PCT Patent Application No. PCT/EP2023/064290 (16 pages).
Altschul et al., "Basic Local Alignment Search Tool," Journal of Molecular Biology, 1990, vol. 215, pp. 403-410.
Altschul et al., "Gapped BLAST and PSI-BLAST: a new generation of protein database search programs," Nucleic Acids Research, 1997, vol. 25, No. 17, pp. 3389-3402.
Brudno et al., "Glocal alignment: finding rearrangements during alignment," Bioinformatics, 2003, vol. 19, Suppl. 1, pp. i54-i62.
Bryson et al., "Prediction of Immunogenicity of Therapeutic Proteins: Validity of Computational Tools," Biodrugs, 2010, vol. 24, Article No. 1, pp. 1-8.
Guo et al., "C5a, a Therapeutic Target in Sepsis," Recent Patents on Anti-Infective Drug Discovery, 2006, vol. 1, No. 1, pp. 57-65.
Holgate et al., "Circumventing immunogenicity in the development of therapeutic antibodies," IDrugs, 2009, vol. 12, No. 4, pp. 233-237.
Hu et al., "Large-scale mammalian cell culture," Current Opinion in Biotechnology, 1997, vol. 8, pp. 148-153.
Karlin et al., "Applications and statistics for multiple high-scoring segments in molecular sequences," Proceedings of the National Academy of Sciences of the United States of America, Jun. 1993, vol. 90, pp. 5873-5877.
Klos et al., "Detection of native human complement components C3 and C5 and their primary activation peptides C3a and C5a (anaphylatoxic peptides) by ELISAs with monoclonal antibodies," Journal of Immunological Methods, 1988, vol. 111, pp. 241-252.
Larkin et al., "Clustal Wand Clustal X version 2.0," Bioinformatics, 2007, vol. 23, No. 21, pp. 2947-2948.
Perry et al., "New Approaches to Prediction of Immune Responses to Therapeutic Proteins during Preclinical Development," Drugs in R & D, 2008, vol. 9, No. 6, pp. 385-396.
Strainic et al., "Absence of signaling into CD4+ cells via C3aR and C5aR enables autoinductive TGF-β1 signaling and induction of Foxp3+ regulatory T cells," Nature Immunology, Feb. 2013, vol. 14, No. 2, pp. 162-171.
Thompson et al., "Clustal W: improving the sensitivity of progressive multiple sequence alignment through sequence weighting, position-specific gap penalties and weight matrix choice," Nucleic Acids Research, 1994, vol. 22, No. 22, pp. 4673-4680.
Xu et al., "Interleukin-17 and its expanding biological functions," Cellular & Molecular Immunology, 2010, vol. 7, pp. 164-174.

\* cited by examiner

TREATMENT OF PNEUMONIA AND ARDS WITH INHIBITORS OF C5a AND IL-6 ACTIVITY

The present invention relates to an inhibitor of C5a activity and an inhibitor of IL-6 activity for use in the treatment of infectious pneumonia and infectious acute respiratory distress syndrome (ARDS). In further aspects administration regimes and kit of parts are referred to.

SEQUENCE LISTING

The present application contains a Sequence Listing which has been submitted electronically in XML format. The contents of the electronic XML Sequence Listing, (Date of creation: May 26, 2023; Size: 49,219 bytes; Name: 180399-010600US-Sequence_Listing.xml), is herein incorporated by reference in its entirety.

BACKGROUND OF THE INVENTION

C5a

C5a is a 74 amino acid spanning split product of its "mother molecule" C5 and represents one endpoint of the complement activation cascade. It can be generated through activation of at least three well-described pathways (the alternative, the classical and the MBL pathway). All pathways merge at the level of C3, forming the C5- or alternative C5 convertase leading to cleavage of C5 into C5a and C5b. The latter binds with C6, C7, C8 and multiple C9 molecules ultimately leading to formation of pores in e.g. bacterial membranes (terminal Membrane Attack Complex=MAC). C5a is generated when the complement system is activated in settings of inflammation and other immunological and inflammatory disorders/diseases.

Among the complement activation products, C5a is one of the most potent inflammatory peptides, with a broad spectrum of functions (Guo and Ward, 2005). C5a exerts its effects through the high-affinity C5a receptors (C5aR and C5L2) (Ward, 2009). C5aR belongs to the rhodopsin family of G-protein-coupled receptors with seven transmembrane segments; C5L2 has a similar structure but appears not to be G-protein-coupled. It is currently believed that C5a exerts its biological functions primarily through C5a-C5aR interaction. However, some reports demonstrate signaling also through C5L2 activation (Rittirsch and others, 2008).

C5aR is widely expressed on myeloid cells including neutrophils, eosinophils, basophils, and monocytes, and non-myeloid cells in many organs, especially in the lung and liver, indicative of the importance of C5a/C5aR signaling. Widespread up-regulation of C5aR expression occurs during the onset of sepsis, and blockade of C5a/C5aR interaction by anti-C5a, or anti-C5aR antibodies, or C5aR antagonists renders highly protective effects in rodent models of sepsis (Czermak and others, 1999; Huber-Lang and others, 2001; Riedemann and others, 2002).

C5a has been reported to exert numerous pro-inflammatory responses. For example, C5a stimulates the synthesis and release from human leukocytes of pro-inflammatory cytokines such as TNF-α, IL-10, IL-6, IL-8, and macrophage migration inhibitory factor (MIF) (Hopken U et al. 1996. Eur J Immunol 26(5):1103-1109; Riedemann N C et al. 2004. J Immunol 173(2):1355-1359; Strieter R M et al. 1992. Am J Pathol 141(2):397-407). C5a produces a strong synergistic effect with LPS in production of TNF-α, macrophage inflammatory protein (MIP)-2, cytokine-induced neutrophil chemoattractant (CINC)-1, and IL-10 in alveolar epithelial cells (Riedemann N C et al. 2002. J. Immunol. 168(4):1919-1925; Rittirsch D et al. 2008. Nat Rev Immunol 8(10):776-787).

C5a has a variety of biological functions (Guo and Ward, 2005). C5a is a strong chemoattractant for neutrophils and also has chemotactic activity for monocytes and macrophages. C5a causes an oxidative burst (02 consumption) in neutrophils and enhances phagocytosis and release of granular enzymes. C5a has also been found to be a vasodilator. C5a has been shown to be involved in modulation of cytokine expression from various cell types and to enhance expression of adhesion molecule expression on neutrophils. High doses of C5a can lead to nonspecific chemotactic "desensitization" of neutrophils, thereby causing broad dysfunction.

Interleukin-6 (IL-6)

IL-6 has a fundamental role in inflammation, immune regulation, hematopoiesis, host defense, homeostasis, and tissue regeneration. It is produced by a wide range of hematopoietic and somatic cells that influences numerous cell types with multiple biological functions.

IL-6 plays a critical role in the immune response by stimulating the growth and differentiation of T and B cells, as well as promoting the production of antibodies. Further, IL-6 is involved in the acute phase response to injury or infection, promoting inflammation and activating immune cells. Its function in hematopoiesis is to stimulate the production of blood cells in the bone marrow, including red blood cells, white blood cells, and platelets. IL-6 is further involved in the regulation of glucose metabolism and lipid metabolism and has been implicated in various neurological functions, including neuroprotection and neuroinflammation. Furthermore, abnormal IL-6 production has been associated with the development of a wide variety of systemic immune-mediated, chronic diseases, and even neoplasms.

IL-6 transmits its signals through a cell-surface type-I receptor complex, that consists of a ligand-binding glycoprotein termed as IL-6 receptor (IL-6R) and a signal-transducing component gp130. When IL-6 binds to IL-6R, it induces a conformational change that enables the recruitment and assembly of gp130. This leads to the formation of a high-affinity IL-6 receptor complex, which activates intracellular signaling pathways. The downstream signaling pathways activated by the IL-6 receptor complex depend on the cell type and context but can include the JAK-STAT pathway, the PI3K-Akt pathway, and the MAPK pathway.

Two forms of IL-6R are known: a membrane-bound form (mIL-6R) and a soluble form (sIL-6R). The membrane-bound form is found on the surface of cells and is responsible for the high-affinity binding of IL-6. The soluble form is generated by proteolytic cleavage of mIL-6R and can bind to IL-6, forming a complex with gp130 and inducing intracellular signaling. The sIL-6R is capable of activating cells that do not express the membrane-bound form of IL-6R, expanding the range of cells that can respond to IL-6.

The IL-6 receptor is expressed on a wide range of cells, including immune cells, hepatocytes, adipocytes, and neurons.

Corona Virus Infection

Different corona virus outbreaks occurred in the last decades worldwide of which in particular three types of virus resulted in diseases with high mortality rates. The Severe Acute Respiratory Syndrome (SARS), the Middle East Respiratory Syndrome (MERS) and lately Coronavirus disease 2019 (COVID-19). The corona virus responsible for these outbreaks where SARS-CoV, MERS-CoV and SARS-CoV-2, respectively.

COVID-19 typically presents with features of long non-symptomatic latency which might be a main contributing factor to a relatively high transmissibility compared to the other previously occurring deadly coronavirus infections, severe acute respiratory syndrome (SARS) and Middle East respiratory syndrome (MERS). COVID-19 patients typically present with flu-like symptoms such as fever or signs of lower respiratory tract illness including dry cough and shortness of With the progression of disease into a severe form, it often affects multiple organs' functions including the lung, heart, liver, and coagulation system among others. As such, death is typically caused by respiratory failure and multiple organ dysfunctions similar to other viral pneumonia-induced sepsis. Sepsis and ARDS mostly occur in the second week upon disease onset.

Older age, underlying health conditions (e.g. cardiovascular issues) and compromised immune systems are important risk factors for the potential of developing a more severe form of disease onset and worse outcomes. The main comorbidities alongside COVID-19 that are associated with a high death rate are hypertension, diabetes and coronary heart disease.

COVID-19 can be characterized by a dual play of viral inflammation and immune-mediated injury that may result in a "complement storm" event occurring in the progression of corona virus infection, in particular COVID-19.

Anti-C5a therapy for COVID-19 has been disclosed in WO2021/190770 A1 and recently received emergency use authorization (EUA) by the FDA. Likewise, the use of an IL-6 receptor inhibitor (Tocilizumab; also known as Actemra) for the treatment of COVID-19 also received an EUA and BLA from the FDA.

In the present invention the surprising effect of a combined anti-C5a and anti-IL-6 therapy of infectious pneumonia and/or infectious acute respiratory distress syndrome (ARDS) is disclosed.

SUMMARY OF THE INVENTION

In a first aspect, the present invention provides an inhibitor of C5a activity for use in:
 (i) combination with an inhibitor of IL-6 activity in the treatment of infectious pneumonia and/or infectious acute respiratory distress syndrome (ARDS); and/or
 (ii) the treatment of infectious pneumonia and/or infectious acute respiratory distress syndrome (ARDS), wherein the patient is or has been treated with an inhibitor of IL-6 activity.

In a second aspect, the present invention provides an inhibitor of IL-6 activity for use in:
 (i) combination with an inhibitor of C5a activity in the treatment of infectious pneumonia and/or infectious acute respiratory distress syndrome (ARDS); and/or
 (ii) the treatment of infectious pneumonia and/or infectious acute respiratory distress syndrome (ARDS), wherein the patient is or has been treated with an inhibitor of C5a activity.

In a third aspect, the present invention provides a kit of parts comprising an inhibitor of C5a activity and an inhibitor of IL-6 activity.

LIST OF FIGURES

In the following, the content of the figures comprised in this specification is described. In this context please also refer to the detailed description of the invention above and/or below.

FIG. 1: IMP Administrations in Phase III refers to the administration schedule of the investigational medicinal product (IMP). The anti-C5a antibody IFX-1 (vilobelimab) was administered at a dose of 800 mg on several days during the treatment period as indicated in FIG. 1.

Figure 2:
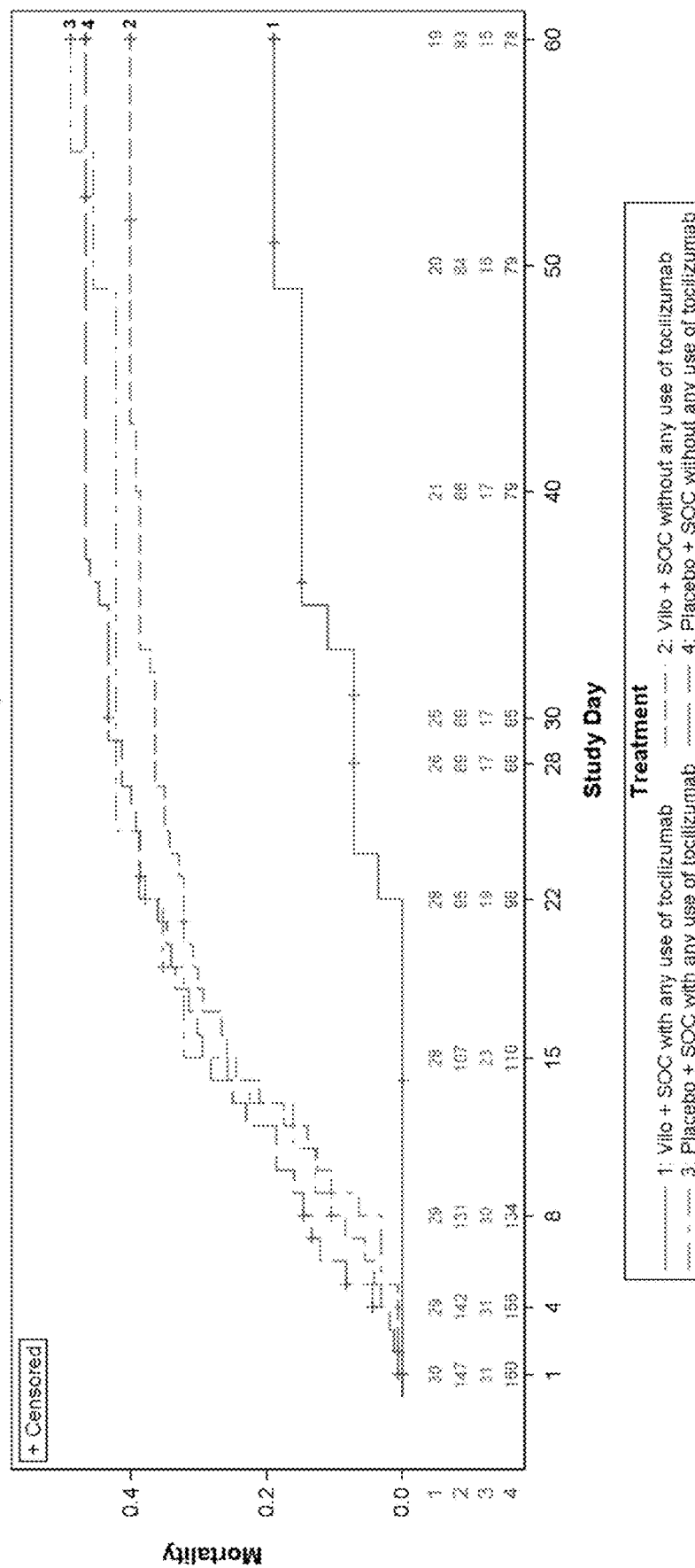

FIG. 2: 60-day all-cause mortality for treatment with vilobelimab and any use of tocilizumab. Line 1: Vilo+SOC with any use of tocilizumab; Line 2: Vilo+SOC without any use of tocilizumab; Line 3: Placebo+SOC with any use of tocvilizumab; Line 4: Placebo+SOC without any use of tocilizumab;

(SOC=Standard of care, Vilo=Vilobelimab)

Figure 3:
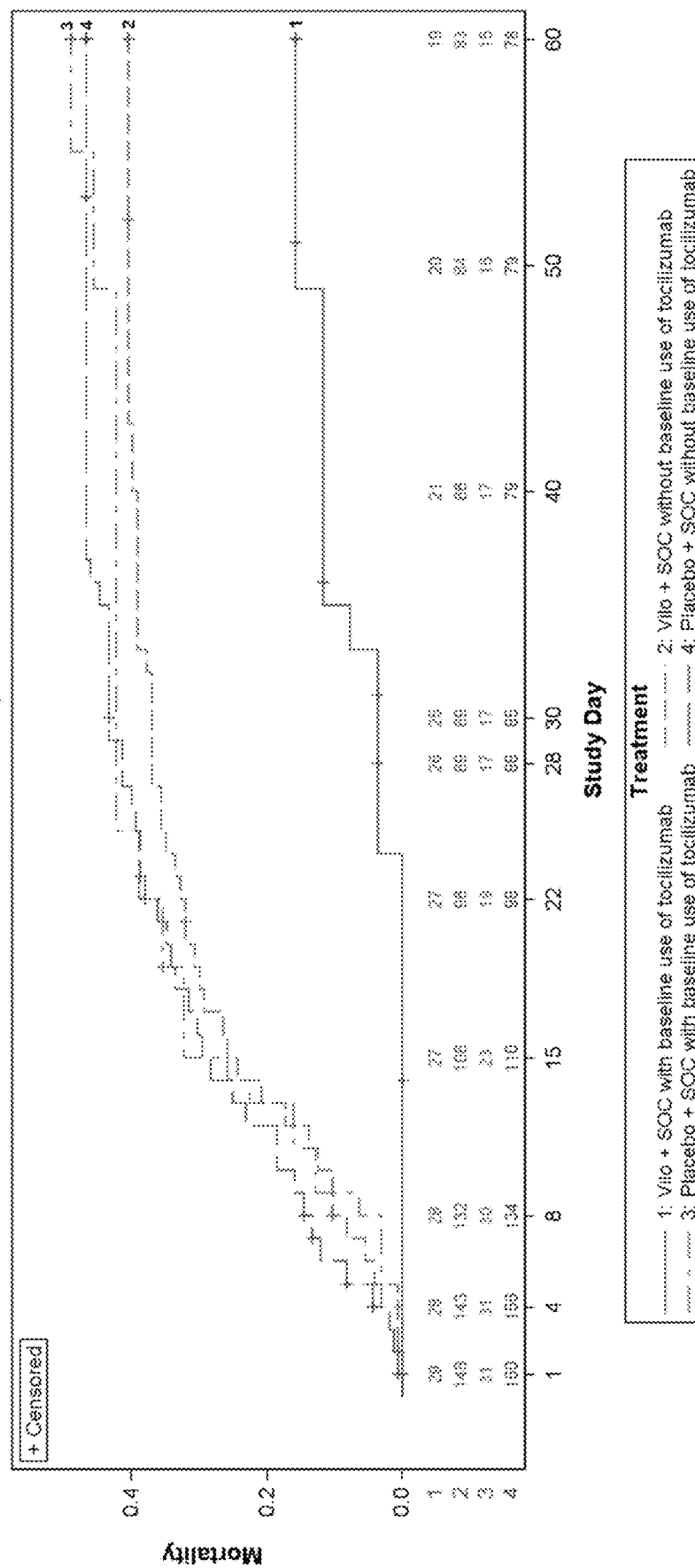

FIG. 3: 60-day all-cause mortality for treatment with vilobelimab and baseline use of tocilizumab. Line 1: Vilo+SOC with baseline use of tocilizumab; Line 2: Vilo+SOC without baseline use of tocilizumab; Line 3: Placebo+SOC with any use of tocilizumab; Line 4: Placebo+SOC without baseline use of tocilizumab;

(SOC=Standard of care, Vilo=Vilobelimab)

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

Sequences: All sequences referred to herein are disclosed in the attached sequence listing that, with its whole content and disclosure, is a part of this specification.

In the context of the present invention, C5a particularly refers to human C5a. Human C5a is a 74 amino acid peptide with the following amino acid sequence:

```
                                              (SEQ ID NO: 1)
TLQKKIEEIA AKYKHSVVKK CCYDGACVNN DETCEQRAAR
ISLGPRCIKA FTECCVVASQ LRANISHKDM QLGR
```

The amino acid sequence of human C5 can be found under the accession number UniProtKB P01031 (C05_HUMAN).

As used herein, the term "inhibitor of C5a activity" refers to any compound that in any way reduces the activity of C5a. This activity reduction can be achieved by directly or indirectly lowering the concentration of C5a, or by reducing the activity of C5a, or by preventing that C5a exerts its effects on one or more of its receptors (e.g. on C5aR or C5L2), or by reducing the concentration or activity of one or more receptors of C5a. Preferred inhibitors of C5a activity are antibodies specifically binding to hC5a.

In the context of the present invention, the expression "C5a receptor" refers to any potential C5a binding ligand on the cell surface, especially to any receptor protein to which C5a may bind and elicit a reaction on said receptor (e.g. activation or inhibition of the receptor). The term "C5a receptor" particularly encompasses the two receptors C5aR and C5L2. Alternative names for C5aR are C5aR1 and CD88. An alternative name for C5L2 is C5aR2.

In the context of the present invention, Interleukin-6 (IL-6) particularly refers to human IL-6. Human IL-6 is an 212 amino acid peptide. The amino acid sequence of human IL-6 can be found under the accession number UniProtKB P05231 (IL6 HUMAN).

As used herein, the term "inhibitor of IL-6 activity" refers to any compound that in any way reduces the activity of IL-6. This activity reduction can be achieved by directly or indirectly lowering the concentration of IL-6, or by reducing the activity of IL-6, or by preventing that IL-6 exerts its effects on one or more of its receptors (e.g. on IL-6R), or by reducing the concentration or activity of one or more receptors of IL-6. Preferred inhibitors of IL-6 activity are antibodies specifically binding to IL-6 or IL-6R, preferably IL-6R.

In the context of the present invention, the expression "IL-6 receptor" refers to any potential IL-6 binding ligand, especially to any receptor protein to which IL-6 may bind and elicit a reaction on said receptor (e.g. activation or inhibition of the receptor). The term "IL-6 receptor" (IL-6R; sometimes referred to as CD126) particularly encompasses the two receptor forms sIL-6R and mIL-6R.

As used herein, a first compound (e.g. an antibody or antigen-binding fragment thereof) is considered to "bind" to a second compound (e.g. a target protein), if it has a dissociation constant $K_d$ to said second compound of 1 mM or less, preferably 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a compound (e.g an antibody or antigen-binding fragment thereof) binds stronger to a target such as an epitope for which it is specific compared to the binding to another target. A compound binds stronger to a first target compared to a second target, if it binds to the first target with a dissociation constant ($K_d$) which is lower than the dissociation constant for the second target. Preferably the dissociation constant ($K_d$) for the target to which the compound binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the compound does not bind specifically.

As used herein, the term "$K_d$" (usually measured in "mol/L", sometimes abbreviated as "M") is intended to refer to the dissociation equilibrium constant of the particular interaction between a binding moiety (e.g. an antibody or antigen-binding fragment thereof) and a target molecule (e.g. an antigen or epitope thereof).

Methods for determining binding affinities of compounds, i.e. for determining the dissociation constant $K_d$, are known to a person of ordinary skill in the art and can be selected for instance from the following methods known in the art: Surface Plasmon Resonance (SPR) based technology, Biolayer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Typically, the dissociation constant $K_d$ is determined at 20° C., 25° C., 30° C., or 37° C. If not specifically indicated otherwise, the $K_d$ values recited herein are determined by surface plasmon resonance spectroscopy (Biacore™) at room temperature (25° C.).

Typically, antibodies and antigen-binding fragments thereof according to the invention bind with a sufficient binding affinity to their target, for example, with a Kd value of between 500 nM-1 pM, i.e. 500 nM, 450 nM, 400 nM, 350 nM, 300 nM, 250 nM, 200 nM, 150 nM, 100 nM, 50 nM, 10 nM, 1 nM, 900 pM, 800 pM, 700 pM, 600 pM, 500 pM, 400 pM, 300 pM, 200 pM, 100 pM, 50 pM, 1 pM.

An "epitope", also known as antigenic determinant, is the part of a macromolecule that is recognized by the immune system, specifically by antibodies, B cells, or T cells. As used herein, an "epitope" is the part of a macromolecule capable of binding to a compound (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

A "paratope" is the part of an antibody that binds to the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, antibodies expressed in eukaryotes (e.g. CHO cells), glycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "CDR" or "complementarity determining region" refers to the non-contiguous antigen binding sites found within the variable region of both heavy and light chain polypeptides (sometimes referred to as LCDR or HCDR). CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The CDRs listed in Table 1 were defined in accordance with Kabat 1991.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those skilled in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1 (Heap C. J. et al. (2005); J. Gen. Virol. 86:1791-1800). Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007 (Qiu X. Q. et al. (2007); Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope. The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgA1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen-binding site derived from another species, e.g. mouse. Moreover, antibodies of the invention include humanized molecules in which the antigen-binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, Frontiers in Bioscience, 13:1619-1633, the content of which is herein incorporated by reference in its entirety. The review article by Almagro & Fransson is briefly summarized in US 2012/0231008 A1 which is the national stage entry of international patent application WO 2011/063980 A1. The contents of US 2012/0231008 A1 and WO 2011/063980 A1 are herein incorporated by reference in their entirety.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies described herein), and epitope-binding fragments of any of the above.

The antibodies described herein are preferably isolated. An "isolated antibody" as used herein, is intended to refer to an antibody which is substantially free of other antibodies having different antigenic specificities (e.g., an isolated antibody that specifically binds to C5a is substantially free of antibodies that specifically bind antigens other than C5a). An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. In one embodiment of the invention, a combination of "isolated" monoclonal antibodies relates to antibodies having different specificities and being combined in a well-defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

Vilobelimab (sometimes referred to as IFX-1; InflaRx GmbH, Germany) is an antibody specifically binding to C5a. The CDR sequences and FR sequences of IFX-1 are disclosed in WO 2011/063980 A1 (in Table 4 on page 51), the content of which is hereby incorporated by reference in its entirety. The affinity ($K_d$) and blocking activity is disclosed in WO 2011/063980 A1 (in Table 3 on pages 49-50), the content of which is hereby incorporated by reference in its entirety.

BNJ364, BNJ367, BNJ371, BNJ378, BNJ366, BNJ369, BNJ381 and BNJ383 are antibodies specifically binding to C5a. The CDR sequences and FR sequences of these antibodies are disclosed in WO 2011/137395 A1 (in Table 2 starting on page 55), the content of which is incorporated by reference in its entirety.

MEDI-7814 (MedImmune) is a recombinant humanized anti-C5a antibody. The crystal structure of the human C5a in complex with MED17814 is available in the RCSB Protein Data Bank under 4UU9 (DOI: 10.2210/pdb4uu9/pdb).

ALXN-1007 (Alexion) is a humanized anti-C5a antibody.

Tocilizumab is a monoclonal antibody specifically binding to the IL-6 receptor (IL-6R). Tocilizumab (brand name Actemra) binds to soluble as well as membrane bound IL-6 receptor (sIL-6R and mIL-6R respectively). Tocilizumab is effective in blocking downstream IL-6 signalling.

Sarilumab (brand name Kevzara) is a further antibody binding to IL-6R that is suitable to exercise the invention. Sarilumab is a human monoclonal antibody binding to the IL-6 receptor.

Levilimab is a fully human monoclonal antibody acting against the interleukin-6 receptor (IL-6R), developed by Biocad, for the treatment of rheumatoid arthritis. Levilimab targets membrane bound and soluble IL-6 receptor.

Vobarilizumab (synonym ALX-0061) is an high affinity anti-IL-6R bispecific nanobody further targeting albumin to extend half-life.

Siltuximab (brand name Sylvant) is a chimeric monoclonal antibody that binds to interleukin-6 (IL-6), preventing binding to soluble and membrane bound interleukin-6 receptors. Siltuximab is FDA-approved for treatment of patients with idiopathic multicentric Castleman's disease (iMCD) who do not have human immunodeficiency virus (HIV) or human herpesvirus-8 (HHV-8).

Sirukumab is a human monoclonal antibody specifically binding to IL-6. Sirukumab is under development for the treatment of rheumatoid arthritis.

Olokizumab is a humanized monoclonal antibody specifically binding to IL-6. Olokizumab has been tested for treatment of rheumatoid arthritis and has been used as an emergency experimental cytokine storm COVID-19 treatment.

Elsilimomab is a monoclonal antibody that targets and blocks IL-6. Elsilimomab has been under development for treatment of lymphoma and myeloma.

Clazakizumab is a humanized monoclonal antibody directed against IL-6. Clazakizumab has been under development for treatment of psoriatic arthritis.

PF-4236921 (sometimes referred to as PF-04236921) is an anti-IL-6 monoclonal antibody that has been under development for the treatment of rheumatoid arthritis, systemic lupus erythematosus and Crohn's disease.

EBI-031 (sometimes referred to as RG-6179) is a humanised monoclonal antibody that specifically binds to IL-6.

As used herein, a "patient" means any mammal or bird who may benefit from a treatment with the compound described herein (i.e. with an inhibitor of C5a activity described herein). Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The term "active agent" as used herein, refers to any therapeutic activity an agent may exhibit.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides an inhibitor of C5a activity for use in:
 (i) combination with an inhibitor of IL-6 activity in the treatment of infectious pneumonia and/or infectious acute respiratory distress syndrome (ARDS); and/or
 (ii) the treatment of infectious pneumonia and/or infectious acute respiratory distress syndrome (ARDS), wherein the patient is or has been treated with an inhibitor of IL-6 activity.

In combination treatment the inhibitor of C5a activity and the inhibitor of IL-6 activity are preferably administered within the half-life of the other inhibitor. For example, if an inhibitor of C5a activity with a half-life of about 4 days and an inhibitor of IL-6 activity with a half-life of about 13 days is used, then the inhibitor of IL-6 activity would be administered within about 3 days after the administration of the inhibitor of C5a activity or if the inhibitor of IL-6 activity is administered first, the inhibitor of C5a activity is administered within 13 days after the inhibitor of IL-6 activity. Thus an overlap between the action of both inhibitors should exist in combination treatment.

In a preferred embodiment the inhibitor of C5a activity and the inhibitor of IL-6 activity are preferably administered within 1-5 (i.e. 1, 2, 3, 4 or 5) half-lives of the other inhibitor.

In a preferred embodiment of the first aspect of the invention the inhibitor of C5a activity and the inhibitor of IL-6 activity are administered on the same day.

In a preferred embodiment of the first aspect of the invention the inhibitor of IL-6 activity is administered within 1, 2, 3, 4, 5, 6, 7, 8, 9, 10, 11, 12, 13 or 14 days prior or after the administration of the inhibitor of C5a activity.

In a preferred embodiment of the first aspect of the invention the inhibitor of C5a activity is administered within 1, 2, 3, 4, 5, 6, 7, 8, 9, 10, 11, 12, 13 or 14 days prior or after the administration of the inhibitor of IL-6 activity.

The patients benefiting most from the use of the inhibitor of C5a activity in the treatment of infectious pneumonia and/or infectious acute respiratory distress syndrome (ARDS) are patients that are or have been treated with an inhibitor of IL-6 activity. In a preferred embodiment the inhibitor of IL-6 activity is or has been administered to the patient within a time-window so that there is an overlap between the action of the inhibitor of IL-6 activity and the inhibitor of C5a activity, at least with regard to the administration of the first dose of the inhibitor of C5a activity.

In a second aspect, the present invention provides an inhibitor of IL-6 activity for use in:
 (i) combination with an inhibitor of C5a activity in the treatment of infectious pneumonia and/or infectious acute respiratory distress syndrome (ARDS); and/or
 (ii) the treatment of infectious pneumonia and/or infectious acute respiratory distress syndrome (ARDS), wherein the patient is or has been treated with an inhibitor of C5a activity.

In combination treatment the inhibitor of IL-6 activity and the inhibitor of C5a activity are preferably administered within the half-life of the other inhibitor. For example, if an inhibitor of IL-6 activity with a half-life of about 13 days and an inhibitor of C5a activity with a half-life of about 4 days is used, then the inhibitor of IL-6 activity would be administered within about 4 days after the administration of the inhibitor of C5a activity or if the inhibitor of IL-6 activity is administered first, the inhibitor of C5a activity is administered within 13 days after the inhibitor of IL-6 activity. Thus an overlap between the action of both inhibitors should exist in combination treatment.

In a preferred embodiment of the first aspect of the invention the inhibitor of IL-6 activity and the inhibitor of C5a activity are administered on the same day.

In a preferred embodiment of the first aspect of the invention the inhibitor of IL-6 activity is administered within 1, 2, 3, 4, 5, 6, 7, 8, 9, 10, 11, 12, 13 or 14 days after the administration of the inhibitor of C5a activity.

In a preferred embodiment of the first aspect of the invention the inhibitor of C5a activity is administered within 1, 2, 3, 4, 5, 6, 7, 8, 9, 10, 11, 12, 13 or 14 days after the administration of the inhibitor of IL-6 activity.

The patients benefiting most from the use of the inhibitor of IL-6 activity in the treatment of infectious pneumonia and/or infectious acute respiratory distress syndrome (ARDS) are patients that are or have been treated with an inhibitor of C5a activity. In a preferred embodiment the inhibitor of C5a activity is or has been administered to the patient within a time-window so that there is an overlap between the action of the inhibitor of IL-6 activity and the inhibitor of C5a activity, at least with regard to the administration of the first dose of the inhibitor of IL-6 activity.

Inhibitors of IL-6 Activity

In a preferred embodiment of all aspects of the present invention, the inhibitor of IL-6 activity specifically binds to IL-6 or the IL-6 receptor. In a preferred embodiment the inhibitor of IL-6 activity comprises a protein ligand. In a preferred embodiment the inhibitor of IL-6 activity is a protein ligand. In a preferred embodiment the inhibitor of IL-6 activity is an antibody or antigen binding fragment thereof specifically binding to the IL-6 receptor. In a preferred embodiment the inhibitor of IL-6 activity is an antibody or antigen binding fragment thereof specifically binding to IL-6.

In a preferred embodiment according to all aspects of the invention the inhibitor of IL-6 activity is specifically binding to IL-6R, preferably selected from Tocilizumab, Sarilumab, Levilimab and Vobarilizumab. Preferably the inhibitor of IL-6R is Tocilizumab.

In a preferred embodiment according to all aspects of the invention the inhibitor of IL-6 activity is specifically binding to IL-6R, preferably selected from Siltuximab, Sirukumab, Olokizumab, Elsilimomab, Clazakinumab, PF-423691 and EBI-031.

Inhibitors of C5a Activity

In a preferred embodiment of all aspects of the invention, the inhibitor of C5a activity binds specifically to C5a or to the C5a receptor (C5aR). In a preferred embodiment, the inhibitor of C5a activity binds specifically to C5a. In a preferred embodiment, the inhibitor of C5a activity binds specifically to C5aR. In a preferred embodiment the inhibitor of C5a activity comprises a protein ligand specifically binding to C5a or the C5aR. In a preferred embodiment the inhibitor of C5a activity comprises a protein ligand specifically binding to C5a. In a preferred embodiment the inhibitor of C5a activity comprises a protein ligand specifically binding to C5aR.

In a preferred embodiment the inhibitor of C5a activity, is a small molecule C5aR antagonist. Suitable small molecule C5aR antagonists are known in the art and can inter alia be found in WO 2020/182384 A1, which is incorporated by reference herein. Methods for preparing the small molecule C5aR antagonists can be found in WO 2020/182384 A1.

In a preferred embodiment the inhibitor of C5a activity is a small molecule having the general formula (I)

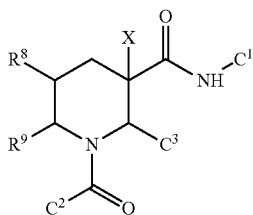

and pharmaceutically acceptable salts, hydrates and rotamers thereof;

wherein $C^1$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^1$ substituents;

$C^2$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^2$ substituents;

$C^3$ is selected from the group consisting of $C_{1-8}$ alkyl or heteroalkyl, $C_{3-8}$ cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-$C_{1-4}$ alkyl, wherein the heteroalkyl group has from 1-3 heteroatoms selected from N, O and S, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1 to 3 $R^3$ substituents;

each $R^1$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aC(O)NR^aR^b$, —$NR^aR^b$, —$OR^a$, and —S(O)$_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^c$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;

each $R^2$ is independently selected from the group consisting of halogen, —CN, —$NO_2$, —$R^f$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR^dR^e$, —$NR^dR^e$, —$OR^d$, and —S(O)$_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each R is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and/or cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;

each $R^3$ is independently selected from the group consisting of halogen, —CN, —$R^i$, —$CO_2R^g$, —$CONR^gR^h$, —C(O)$R^g$, —C(O)$R^i$, —OC(O)$NR^gR^h$, —$NR^hC(O)R^g$, —$NR^hCO_2R^i$, —$NR^gC(O)NR^gR^h$, —$NR^gR^h$, —$OR^g$, —$OR^i$, —S(O)$_2NR^gR^h$, —$X^4$—$R^j$, —NH—$X^4$—$R^j$, —O—$X^4$—$R^j$, —$X^4$—$NR^gR^h$, —$X^4$—$NHR^j$, —$X^4$—$CONR^gR^h$, —$X^4$—$NR^hC(O)R^g$, —$X^4$—$CO_2R^g$, —O—$X^4$—$CO_2R^g$, —NH—$X^4$—$CO_2R^g$, —$X^4$—$NR^hCO_2R^i$, —O—$X^4$—$NR^hCO_2R$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl or heteroalkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each $R^i$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, imidazolyl, pyrimidinyl, pyrrolinyl, pyrrolyl, piperidinyl, morpholinyl, tetrahydrofuranyl, tetrahydropyranyl, and S,S-dioxo-tetrahydrothiopyranyl, and wherein the aliphatic and/or cyclic portions of $R^g$, $R^h$, $R^i$ and $R^j$ are optionally further substituted with from one to three halogen, methyl, $CF_3$, hydroxy, $C_{1-4}$ alkoxy, $C_{1-4}$ alkoxy-$C_{1-4}$ alkyl, —C(O)O—$C_{1-8}$ alkyl, amino, alkylamino and dialkylamino groups, and optionally when two $R^3$ groups are on adjacent atoms, they are combined to form a five- or six-membered ring;

X is hydrogen or $CH_3$; and $R^8$ and $R^9$ are independently from each other selected from the group consisting of hydrogen, halogen, $C_1$-$C_8$ alkyl, $C_1$-$C_8$ haloalkyl, and $C_1$-$C_8$ alkoxy or $R^8$ and $R^9$ are combined to form a fused saturated or unsaturated mono- or multi-ring carbocycle in which one or more of the ring carbon atoms may be replaced independently from each other by N, S, or O, with the proviso that at least one of $R^8$ and $R^9$ is not hydrogen.

In a preferred embodiment the inhibitor of C5a activity is a small molecule C5aR antagonist having the general formula (I) as indicated above and wherein $R^8$ and/or $R^9$ is hydrogen.

In a preferred embodiment the inhibitor of C5a activity is selected from:

INF004: (2R,3S)-2-(4-(cyclopentylamino)phenyl)-1-(2-fluoro-6-methylbenzoyl)-N-(4-methyl-3-(trifluoromethyl)phenyl)-1,2,3,4-tetrahydroquinoline-3-carboxamide INF011: (2R,3S)-1-(2-fluoro-6-methylbenzoyl)-N-(4-methyl-3-(trifluoromethyl)phenyl)-2-(4-((tetrahydro-2H-pyran-4-yl)amino)phenyl)-1,2,3,4-tetrahydroquinoline-3-carboxamide INF014: (2R,3S)-1-(2-chlorobenzoyl)-2-(4-(cyclopentylamino)phenyl)-N-(4-(hydroxymethyl)-3-(trifluoromethyl)phenyl)-1,2,3,4-tetrahydroquinoline-3-carboxamide INF015: (2R,3S)-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF022: (2R,3S)-2-(4-(cyclopentylamino)phenyl)-6-fluoro-1-(2-fluoro-6-methylbenzoyl)-N-(4-methyl-3-(trifluoromethyl)phenyl)-1,2,3,4-tetrahydroquinoline-3-carboxamide INF023: (2R,3S)-2-(4-(cyclopentylamino)phenyl)-1-(2-fluoro-6-methylbenzoyl)-6-methyl-N-(4-methyl-3-(trifluoromethyl)phenyl)-1,2,3,4-tetrahydroquinoline-3-carboxamide INF024: (2R,3S)-2-(4-(cyclopentylamino)phenyl)-1-(2-fluoro-6-methylbenzoyl)-6-methoxy-N-(4-methyl-3-(trifluoromethyl)phenyl)-1,2,3,4-tetrahydroquinoline-3-carboxamide INF025: (2R,3S)-2-(4-(cyclopentylamino)phenyl)-6,7-difluoro-1-(2-fluoro-6-methylbenzoyl)-N-(4-methyl-3-(trifluoromethyl)phenyl)-1,2,3,4-tetrahydroquinoline-3-carboxamide INF030: (2R,3S)-1-(2-fluoro-6-methylbenzoyl)-N-(4-(hydroxymethyl)-3-(trifluoromethyl)phenyl)-2-(4-((tetrahydro-2H-pyran-4-yl)amino)phenyl)-1,2,3,4-tetrahydroquinoline-3-carboxamide INF033: (2R,3S)-2-(4-(cyclopentylamino)phenyl)-1-(2-fluoro-6-methylbenzoyl)-N-(4-hydroxy-3-(trifluoromethyl)phenyl)-1,2,3,4-tetrahydroquinoline-3-carboxamide INF034: (2R,3S)-1-(2-fluoro-6-methylbenzoyl)-2-(4-(3-hydroxy-3-methylbutyl)phenyl)-N-(4-methyl-3-(trifluoromethyl)phenyl)-1,2,3,4-tetrahydroquinoline-3-carboxamide INF035: (2R,3S)-2-(4-(cyclopentylamino)phenyl)-1-(2-fluoro-6-methylbenzoyl)-N-(3-(hydroxymethyl)phenyl)-1,2,3,4-tetrahydroquinoline-3-carboxamide INF038: (2R,3S)-1-(2-fluoro-6-methylbenzoyl)-N-(4-(hydroxymethyl)-3-(trifluoromethyl)phenyl)-2-phenyl-1,2,3,4-tetrahydroquinoline-3-carboxamide INF039: (2R,3S)-2-(4-(cyclopentylamino)phenyl)-6-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF040: (2R,3S)-2-(4-(cyclopentylamino)phenyl)-N-(4-(hydroxymethyl)-3-(trifluoromethyl)phenyl)-1-(2-methylbenzoyl)-1,2,3,4-tetrahydroquinoline-3-carboxamide INF041: (2R,3S)-2-(4-(cyclopentylamino)phenyl)-1-(2-fluorobenzoyl)-N-(4-(hydroxymethyl)-3-(trifluoromethyl)phenyl)-1,2,3,4-tetrahydroquinoline-3-carboxamide INF045: (2R,3S)-2-(4-(cyclopentylamino)phenyl)-5-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF046: (2R,3S)-2-(4-(cyclopentylamino)phenyl)-7-fluoro-1-(2-fluoro-6-methylbenzoyl)-N-(4-(hydroxymethyl)-3-(trifluoromethyl)phenyl)-1,2,3,4-tetrahydroquinoline-3-carboxamide INF047: (2R,3S)-6-chloro-2-(4-(cyclopentylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF048: (2R,3S)-1-(2-fluoro-6-methylbenzoyl)-2-(4-(3-hydroxy-3-methylbutyl)phenyl)-N-(4-(hydroxymethyl)-3-(trifluoromethyl)phenyl)-1,2,3,4-tetrahydroquinoline-3-carboxamide INF049: (2R,3S)-1-(2-fluoro-6-methylbenzoyl)-N-(4-(hydroxymethyl)-3-(trifluoromethyl)phenyl)-2-(4-(isopropylamino)phenyl)-1,2,3,4-tetrahydroquinoline-3-carboxamide INF050: (2R,3S)-2-(4-(cyclobutylamino)phenyl)-1-(2-fluoro-6-methylbenzoyl)-N-(4-(hydroxymethyl)-3-(trifluoromethyl)phenyl)-1,2,3,4-tetrahydroquinoline-3-carboxamide INF051: (2R,3S)-1-(2-fluoro-6-methylbenzoyl)-2-(4-((2-hydroxy-2-methylpropyl)amino)phenyl)-N-(4-(hydroxymethyl)-3-(trifluoromethyl)phenyl)-1,2,3,4-tetrahydroquinoline-3-carboxamide INF052: (2R,3S,5R)-2-(4-(cyclopentylamino)phenyl)-1-(2,6-difluorobenzoyl)-N-(4-methyl-3-(trifluoromethyl)phenyl)-5-(trifluoromethyl)piperidine-3-carboxamide INF053: (2R,3S,5R)-2-(4-(cyclopentylamino)phenyl)-1-(2,6-dimethylbenzoyl)-N-(4-methyl-3-(trifluoromethyl)phenyl)-5-(trifluoromethyl)piperidine-3-carboxamide INF055: (2R,3S)-2-(4-(cyclopentylamino)phenyl)-1-(2-fluoro-6-methylbenzoyl)-N-(4-(hydroxymethyl)-3-(trifluoromethyl)phenyl)-6-(trifluoromethyl)-1,2,3,4-tetrahydroquinoline-3-carboxamide INF056: (2R,3S,5R)-2-(4-(cyclopentylamino)phenyl)-1-(2-fluoro-6-methylbenzoyl)-N-(4-methyl-3-(trifluoromethyl)phenyl)-5-(trifluoromethyl)piperidine-3-carboxamide INF058: (2R,3S)-1-(2-fluoro-6-methylbenzoyl)-2-(4-(2-hydroxy-2-methylpropoxy)phenyl)-N-(4-methyl-3-(trifluoromethyl)phenyl)-1,2,3,4-tetrahydroquinoline-3-carboxamide INF067: (2R,3S,5R)-2-(4-((cyclopentyl-1-d)amino)phenyl)-1-(2,6-difluorobenzoyl)-N-(4-methyl-3-(trifluoromethyl)phenyl)-5-(trifluoromethyl)piperidine-3-carboxamide INF068: (2R,3S,5R)-2-(4-(cyclopentylamino)phenyl)-1-(2,6-difluorobenzoyl)-N-(4-hydroxy-3-(trifluoromethyl)phenyl)-5-(trifluoromethyl)piperidine-3-carboxamide INF069: (2R,3S,5R)-2-(4-(cyclopentylamino)phenyl)-1-(2,6-difluorobenzoyl)-N-(4-(hydroxymethyl)-3-(trifluoromethyl)phenyl)-5-(trifluoromethyl)piperidine-3-carboxamide INF070: (2R,3S,5R)-1-(2,6-difluorobenzoyl)-N-(4-methyl-3-(trifluoromethyl)phenyl)-2-(4-((tetrahydro-2H-pyran-4-yl)amino)phenyl)-5-(trifluoromethyl)piperidine-3-carboxamide INF071: (2R,3S,5R)—N-(3-chloro-4-methylphenyl)-2-(4-(cyclopentylamino)phenyl)-1-(2,6-difluorobenzoyl)-5-(trifluoromethyl)piperidine-3-carboxamide INF072: (2R,3S,5R)—N-(3-chloro-4-hydroxyphenyl)-2-(4-(cyclopentylamino)phenyl)-1-(2,6-difluorobenzoyl)-5-(trifluoromethyl)piperidine-3-carboxamide INF075: (2R,3S,5R)-1-(2-chloro-6-fluorobenzoyl)-2-(4-(cyclopentylamino)phenyl)-N-(4-methyl-3-(trifluoromethyl)phenyl)-5-(trifluoromethyl)piperidine-3-carboxamide INF077: (2R,3S,5R)—N-(4-chloro-3-(trifluoromethyl)phenyl)-2-(4-(cyclopentylamino)phenyl)-1-(2,6-difluorobenzoyl)-5-(trifluoromethyl)piperidine-3-carboxamide INF080: (2R,3S,5R)-2-(4-(cyclopentylamino)phenyl)-N-(3,4-dichlorophenyl)-1-(2,6-difluorobenzoyl)-5-(trifluoromethyl)piperidine-3-carboxamide Methods for preparing these small molecule C5aR antagonists can be found in WO 2020/182384 A1.

In a preferred embodiment the inhibitor of C5a activity is INF052.

In a preferred embodiment the inhibitor of C5a activity is avacopan, having the structure of general formula (II):

(II)

In a preferred embodiment of all aspects of the present invention, the inhibitor of C5a activity is a protein ligand, wherein the protein ligand is an antibody or an antigen binding fragment thereof. More preferably the protein ligand comprises a $V_H$ and a $V_L$ domain of an antibody, a Fab fragment, a Fab' fragment, a heavy chain antibody, a single-domain antibody (sdAb), variable domain of a heavy chain antibody, a VHH, a nanobody, a single-chain variable fragment (scFv), a tandem scFv, or a single-chain diabody.

In a preferred embodiment of all aspects of the present invention, the inhibitor of C5a activity is a protein ligand, wherein the protein ligand is an antibody-like protein, preferably an affibody, anticalin, or an designed ankyrin repeat protein. Antibody-like proteins include without limitation affibodies, anticalins, and designed ankyrin repeat proteins (for review see: Binz H. K. et al. (2005) Engineering novel binding proteins from non-immunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

In a preferred embodiment of all aspects of the present invention, the inhibitor of C5a activity is a protein ligand, wherein the protein ligand is an inhibitory variant of C5a.

In a preferred embodiment of all aspects of the present invention, the inhibitor of C5a activity is a protein ligand, wherein the protein ligand is an inhibitory variant of C5a receptor.

In preferred embodiments of all aspects of the invention, wherein the inhibitor of C5a activity is a protein ligand, preferably an antibody or antigen-binding fragment thereof, specifically binding to a conformational epitope of human C5a formed by (a) amino acid sequences NDETCEQRA (SEQ ID NO: 2) and SHKDMQL (SEQ ID NO: 3) of C5a binds to a conformational epitope of C5a formed by amino acid sequences NDETCEQRA (SEQ ID NO: 2) and SHKDMQL (SEQ ID NO: 3), and binds to at least one amino acid within the amino acid sequence according to SEQ ID NO: 2 and to at least one amino acid within the amino acid sequence according to SEQ ID NO: 3. In other words, the inhibitor of C5a activity according to this preferred embodiment binds at the same time to at least one amino acid within the amino acid sequence according to SEQ ID NO: 2 and to at least one amino acid within the amino acid sequence according to SEQ ID NO: 3. SEQ ID NO: 2 corresponds to amino acids 30-38 of human C5a. SEQ ID NO: 3 corresponds to amino acids 66-72 of human C5a. The amino acid sequence of human C5a is depicted in SEQ ID NO: 1. In more preferred embodiments, the inhibitor of C5a activity binds to at least one of amino acids DETCEQR (SEQ ID NO: 4). SEQ ID NO: 4 corresponds to amino acids 31-37 of human C5a. In more preferred embodiments, the inhibitor of C5a activity binds to at least one of amino acids HKDMQ (SEQ ID NO: 5), more preferably to at least one of amino acids KDM. SEQ ID NO: 5 correspond to amino acids 67-71 of human C5a; the sequence KDM corresponds to amino acids 68-70 of human C5a. In particularly preferred embodiments, the inhibitor of C5a activity binds at the same time to at least one amino acid within the amino acid sequence DETCEQR (SEQ ID NO: 4) and to at least one amino acid within the amino acid sequence KDM.

In a preferred embodiment the specific binding to the amino acids of the conformational epitope is determined by alanine scanning. In a preferred embodiment the conformational epitope is determined by alanine scanning.

The skilled person is aware of assays for screening antibodies binding to the specified conformational epitope. One such suitable assay is described in the following: In 3-D structure of C5a obtained from computer modeling method, the spatial epitopes containing peptide C5a 28-40 (VNN-DETCEQRAAR, SEQ ID NO: 53) and C5a peptide 65-70 (ISHKDM, SEQ ID NO: 54) can be viewed as random coils. When the two peptides are linked by a flexible peptide linker, GGGGS (SEQ ID NO: 55), the spatial epitopes is reconstructed resembling the parent antigen conformation, as the weak hydrophobic interaction from the two peptides ensures a pocket-shape conformation. Computer modeling analysis of the peptide NH$_2$-28-40-Linker(GGGGS)-65-70-COOH maintains the same conformation as the parent antigen. This new 24-AA peptide can be synthesized and conjugated with keyhole limpet hemocyanin (KLH) to form an immunogen to immunize mice, and the traditional hybridoma technology can be subsequently applied to obtain INab308 and INab708 using the new 24-AA peptide based ELISA as a screening tool. A 96-well ELISA plate is coated with 1-2 pug/mL synthetic peptides with the conformational epitope at 4° C. overnight. After being blocked with 5% nonfat milk in PBS at 37° C. for 1 h, 50 µL of culture media of the hybridoma growing clones are added to each well and incubated at 37° C. for 1 h, followed by 100 µL of goat anti-mouse antibody labeled with horseradish peroxidase (HRP) for 1 h. The peroxidase reaction is developed with color development solution containing 5.5 mM o-phenylene-diamine hydrochloride (OPD) and 8.5 mM H$_2$O$_2$. The light absorbance is measured at 492 nm with an ELISA reader.

In a preferred embodiment of all aspects of the present invention wherein the inhibitor of C5a activity is an antibody or antigen-binding fragment thereof specifically binding to C5a comprising a variable domain of a heavy chain (V$_H$) and a variable domain of a light chain (V$_L$).

Preferably the V$_L$ comprises a light chain CDR3 sequence CQQSNEDPYT as set forth in SEQ ID NO: 6. In a preferred embodiment the V$_L$ further comprises a FR2 sequence WYQQKPGQPPKLL as set forth in SEQ ID NO: 8 or SEQ ID NO: 39.

Preferably the V$_L$ comprises a light chain CDR3 sequence CQQNNEDPLT as set forth in SEQ ID NO: 7. In a preferred embodiment the V$_L$ further comprises a FR2 sequence WYQQKPGQPPKLL as set forth in SEQ ID NO: 8 or SEQ ID NO: 39.

In a preferred embodiment the inhibitor of C5a activity further comprises at least one of the following sequences:
(i) a heavy chain CDR2 sequence IDPSDSESRLDQ according to SEQ ID NO: 9;
(ii) a heavy chain CDR2 sequence ILPGSGSTNYNE according to SEQ ID NO: 10;
(iii) a light chain CDR2 sequence IYAASNL according to SEQ ID NO: 11;
(iv) a light chain CDR2 sequence IYAASNL according to SEQ ID NO: 12;
(v) a heavy chain CDR1 sequence CKASGYSFTTFWMD according to SEQ ID NO: 13;
(vi) a heavy chain CDR1 sequence CKATGNTFSGYWIE according to SEQ ID NO: 14;
(vii) a light chain CDR1 sequence CKASQSVDYDGDSYMK according to SEQ ID NO: 15;
(viii) a light chain CDR1 sequence CKASQSVDYDGDSYMN according to SEQ ID NO: 16;
(ix) a heavy chain CDR3 sequence CARGNDGYYGFAY according to SEQ ID NO: 17; or
(x) a heavy chain CDR3 sequence CTRRG-LYDGSSYFAY according to SEQ ID NO:18.

In a preferred embodiment the inhibitor of C5a activity comprises a light chain CDR3 sequence according to SEQ ID NO: 6, a light chain CDR2 sequence according to SEQ ID NO: 11, a light chain CDR1 sequence according to SEQ ID NO: 15, a heavy chain CDR3 sequence according to SEQ ID NO: 17, a heavy chain CDR2 sequence according to SEQ ID NO: 9, and a heavy chain CDR1 sequence according to SEQ ID NO: 13. In a preferred embodiment the inhibitor of C5a activity further comprises the light chain framework regions (FR) 1 to 4 according to SEQ ID NOs: 19, 8, 20 and 21, respectively; preferably further comprising the heavy chain FR 1 to 4 according to SEQ ID NOs: 23, 24, 25 and 26, respectively. In an alternative preferred embodiment the inhibitor of C5a activity further comprises the light chain framework regions (FR) 1 to 4 according to SEQ ID NOs:37, 39, 41 and 43, respectively; preferably further comprising the heavy chain FR 1 to 4 according to SEQ ID NOs:45, 47, 49 and 51, respectively.

In a preferred embodiment the inhibitor of C5a activity comprises a light chain CDR3 sequence according to SEQ ID NO: 7, a light chain CDR2 sequence according to SEQ ID NO: 12, and a light chain CDR1 sequence according to SEQ ID NO: 16, a heavy chain CDR3 sequence according to SEQ ID NO: 18, a heavy chain CDR2 sequence according to SEQ ID NO: 10, and a heavy chain CDR1 sequence according to SEQ ID NO: 14. In a preferred embodiment the inhibitor of C5a activity further comprises the light chain framework regions (FR) 1 to 4 according to SEQ ID NOs:28, 8, 29 and 30, respectively; preferably further comprising the heavy chain FR 1 to 4 according to SEQ ID NOs:32, 33, 34 and 35, respectively.

In a preferred embodiment the FR sequences have a sequence identity to the herein disclosed FR sequences of at least 99%, at least 98% at least 95%, at least 90%, at least 85%, at least 80% or at least 75% sequence.

In a preferred embodiment according to all aspects of the invention the inhibitor of C5a activity is selected from IFX-1 (vilobelimab), IFX-2, INab708, BNJ364, BNJ367, BNJ371, BNJ378, BNJ366, BNJ369, BNJ381, BNJ383, MEDI-7814 or ALXN-1007, or an antigen-binding fragment thereof.

In a preferred embodiment according to all aspects of the invention the inhibitor of C5a activity is IFX-1 (vilobelimab).

The sequences of IFX-1, INab708 and IFX-2 can be found in Table 1 below.

TABLE 1

FR1, CDR1, FR2, CDR2, FR3, CDR3, and FR4 sequences of VL and VH domains of suitable inhibitors of C5a activity

| IFX-1 (vilobelimab) | |
|---|---|
| SIN Light chain: | SIN Heavy chain: |
| 19 FR1 DIVLTQSPASLAVSLGQRATIS | 23 FR1 QVQLQQSGPQLVRPGTSVKIS |

TABLE 1-continued

FR1, CDR1, FR2, CDR2, FR3, CDR3, and FR4 sequences of VL and VH domains of suitable inhibitors of C5a activity

| | | | |
|---|---|---|---|
| 15 | CDR1<br>CKASQSVDYDGDSYMK | 13 | CDR1<br>CKASGYSFTTFWMD |
| 8 | FR2<br>WYQQKPGQPPKLL | 24 | FR2<br>WVKQRPGQGLEWIGR |
| 11 | CDR2<br>IYAASNL | 9 | CDR2<br>IDPSDSESRLDQ |
| 20 | FR3<br>QSGIPARFSGSGSGTDFTLNIH<br>PVEEEDAATYY | 25 | FR3<br>RFKDRATLTVDKSSSTVYMQLSS<br>PTSEDSAVYY |
| 6 | CDR3<br>CQQSNEDPYT | 17 | CDR3<br>CARGNDGYYGFAY |
| 21 | FR4<br>FGGGTKLEIK | 26 | FR4<br>WGQGTLVTVSSA |
| 22 | VL domain:<br>DIVLTQSPASLAVSLGQRATIS<br>CKASQSVDYDGDSYMKWY QQKP<br>GQPPKLLIYAASNLQSGIPARF<br>SGSGSGTDETLNIHPVEEEDAA<br>TYYCQQSNEDPYTFGGGTKLEI<br>K | 27 | VH domain:<br>QVQLQQSGPQLVRPGTSVKISCK<br>ASGYSFTTFWMDWVKQRPGQGLE<br>WIGRIDPSDSESRLDQRFKDRAT<br>LTVDKSSSTVYMQLSSPTSEDSA<br>VYYCARGNDGYYGFAYWGQGTLV<br>TVSSA |

INab708

| SIN | Light chain | SIN | Heavy chain |
|---|---|---|---|
| 28 | FR1<br>DIVLTQSPASLAVSLGQRATIS | 32 | FR1<br>VQLLESGAELMKPGASVKIS |
| 16 | CDR1<br>CKASQSVDYDGDSYMN | 14 | CDR1<br>CKATGNTFSGYWIE |
| 8 | FR2<br>WY QQKPGQPPKLL | 33 | FR2<br>WVKQRPGHGLEWIGE |
| 12 | CDR2<br>IYAASNL | 10 | CDR2<br>ILPGSGSTNYNE |
| 29 | FR3<br>GSGIPARFSGSGSGTDFTLNIH<br>PVEEEVAATYY | 34 | FR3<br>KFKGKATLTADTSSNTAYMQLSS<br>LTSEDSAVYY |
| 7 | CDR3<br>CQQNNEDPLT | 18 | CDR3<br>CTRRGLYDGSSYFAY |
| 30 | FR4<br>FGAGTLLELK | 35 | FR4<br>WGQGTLVTVSA |
| 31 | VL domain:<br>DIVLTQSPASLAVSLGQRATIS<br>CKASQSVDYDGDSYMNWY QQKP<br>GQPPKLLIYAASNLGSGIPARF<br>SGSGSGTDFTLNIHPVEEEVAA<br>TYYCQQNNEDPLTFGAGTLLEL<br>K | 36 | VH domain<br>VQLLESGAELMKPGASVKISCKA<br>TGNTFSGYWIEWVKQRPGHGLEW<br>IGEILPGSGSTNYNEKFKGKATL<br>TADTSSNTAYMQLSSLTSEDSAV<br>YYCTRRGLYDGSSYFAYWGQGTL<br>VTVSA |

IFX-2

| SIN | Light chain | SIN | Heavy chain |
|---|---|---|---|
| 37 | FR1<br>DIQMTQSPSSLSASVGDRVTIT | 45 | FR1<br>QVQLVQSGAEVKKPGASVKVS |
| 38 | CDR1<br>CKASQSVDYDGDSYMK | 46 | CDR1<br>CKASGYSFTTFWMD |

TABLE 1-continued

FR1, CDR1, FR2, CDR2, FR3, CDR3, and FR4 sequences of VL and VH domains of suitable inhibitors of C5a activity

| | | | | |
|---|---|---|---|---|
| 39 | FR2<br>WYQQKPGKAPKLL | | 47 | FR2<br>WVRQAPGQGLEWIGR |
| 40 | CDR2<br>IYAASNL | | 48 | CDR2<br>IDPSDSESRLDQ |
| 41 | FR3<br>QSGVPSRFSGSGSGTDFTLTIS<br>SLQPEDFATYY | | 49 | FR3<br>RFKDRVTMTVDKSTSTVYMELSS<br>LRSEDTAVYY |
| 42 | CDR3<br>CQQSNEDPYT | | 50 | CDR3<br>CARGNDGYYGFAY |
| 43 | FR4<br>FGQGTKLEIK | | 51 | FR4<br>WGQGTLVTVSS |
| 44 | VL domain:<br>DIQMTQSPSSLSASVGDRVTIT<br>CKASQSVDY DGDSYMKWY QQKP<br>GKAPKLLIYAASNLQSGVPSRF<br>SGSGSGTDFTLTISSLQPEDFA<br>TYYCQQSNEDPYTFGQGTKLEI<br>K | | 52 | VH domain:<br>QVQLVQSGAEVKKPGASVKVSCK<br>ASGYSFTTFWMDWVRQAPGQGLE<br>WIGRIDPSDSESRLDQRFKDRVT<br>MTVDKSTSTVYMELSSLRSEDTA<br>VYYCARGNDGYYGFAYWGQGTLV<br>TVSS |

In a preferred embodiment according to all aspects of the invention the inhibitor of C5a activity is selected from an antibody or antigen binding fragment thereof that competes for binding with any of the antibodies selected from: IFX-1 (vilobelimab), IFX-2, INab708, BNJ364, BNJ367, BNJ371, BNJ378, BNJ366, BNJ369, BNJ381, BNJ383, MEDI-7814 or ALXN-1007.

In a preferred embodiment according to all aspects of the invention the inhibitor of C5a activity is an antibody or antigen-binding fragment thereof that specifically binds to human C5a comprises (i) a light chain variable domain (VL) having at least 99%, at least 98% at least 95%, at least 90%, at least 85%, at least 80%, at least 75% sequence identity with the VL domain according to SEQ ID NO: 22 and (ii) a heavy chain variable domain (VH) having at least 99%, at least 98% at least 95%, at least 90%, at least 85%, at least 80%, at least 75% sequence identity with the VH domain according to SEQ ID NO: 27. In a preferred embodiment the sequence variation does not include the CDR sequences.

In a preferred embodiment according to all aspects of the invention the inhibitor of C5a activity is an antibody or antigen-binding fragment thereof that specifically binds to human C5a comprises (i) a light chain variable domain (VL) according to SEQ ID NO: 22 and (ii) a heavy chain variable domain (VH) according to SEQ ID NO: 27.

In a preferred embodiment according to all aspects of the invention the inhibitor of C5a activity is an antibody or antigen-binding fragment thereof that specifically binds to human C5a comprises (i) a light chain variable domain (VL) having at least 99%, at least 98% at least 95%, at least 90%, at least 85%, at least 80%, at least 75% sequence identity with the VL domain according to SEQ ID NO: 31 and (ii) a heavy chain variable domain (VH) having at least 99%, at least 98% at least 95%, at least 90%, at least 85%, at least 80%, at least 75% sequence identity with the VH domain according to SEQ ID NO: 36. In a preferred embodiment the sequence variation does not include the CDR sequences.

In a preferred embodiment according to all aspects of the invention the inhibitor of C5a activity is an antibody or antigen-binding fragment thereof that specifically binds to human C5a comprises (i) a light chain variable domain (VL) according to SEQ ID NO: 31 and (ii) a heavy chain variable domain (VH) according to SEQ ID NO: 36.

In a preferred embodiment according to all aspects of the invention the inhibitor of C5a activity is an antibody or antigen-binding fragment thereof that specifically binds to human C5a comprises (i) a light chain variable domain (VL) having at least 99%, at least 98% at least 95%, at least 90%, at least 85%, at least 80%, at least 75% sequence identity with the VL domain according to SEQ ID NO: 44 and (ii) a heavy chain variable domain (VH) having at least 99%, at least 98% at least 95%, at least 90%, at least 85%, at least 80%, at least 75% sequence identity with the VH domain according to SEQ ID NO: 52. In a preferred embodiment the sequence variation does not include the CDR sequences.

In a preferred embodiment according to all aspects of the invention the inhibitor of C5a activity is an antibody or antigen-binding fragment thereof that specifically binds to human C5a comprises (i) a light chain variable domain (VL) according to SEQ ID NO: 44 and (ii) a heavy chain variable domain (VH) according to SEQ ID NO: 52.

In a preferred embodiment according to all aspects of the present invention the inhibitors of C5a activity are antibodies or antigen binding fragments thereof disclosed herein comprising one, two or three modified amino acids within the CDR sequences. The modified amino acids are selected from substitution, insertion or deletion, preferably substitution. In a preferred embodiment the one, two or three modified amino acids are conservative amino acid substitutions. "Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative amino acid substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

The inhibitors of C5a activity disclosed herein may freely be combined with the inhibitors of IL-6 activity for the claimed use.

In a preferred embodiment the inhibitor of C5a activity is vilobelimab and the inhibitor of IL-6 activity is tocilizumab.

Infectious Pneumonia and Infectious Acute Respiratory Distress Syndrome (ARDS)

Pneumonia is a medical condition of the lung characterized by inflammation of the lung tissue in particular the aleveoli. Pneumonia can be caused by various pathogens, including bacteria, viruses, fungi, and other microorganisms. The infection causes the alveoli in the lungs to become filled with fluid, pus, and cellular debris, which impairs the lungs' ability to efficiently exchange oxygen and carbon dioxide.

In a preferred embodiment the infectious pneumonia is viral pneumonia, bacterial pneumonia or fungal pneumonia, preferably viral pneumonia or bacterial pneumonia, more preferably viral pneumonia. Viral pneumonia may be caused by various viruses including but not limited to influenza virus A or B, respiratory syncytial virus, and severe acute respiratory syndrome coronavirus 2 (SARS-CoV-2). Preferably the infectious viral pneumonia is caused by SARS-CoV-2.

In a more preferred embodiment the infectious pneumonia is COVID-19 pneumonia, i.e. viral pneumonia caused by SARS-CoV-2 infection.

Acute respiratory distress syndrome (ARDS) is a severe and life-threatening condition that affects the lungs. ARDS is characterized by inflammation and damage to the alveoli. This damage results in increased permeability of the alveolar-capillary membrane, causing fluid leakage into the alveoli impairing their ability to effectively exchange oxygen and carbon dioxide.

In a preferred embodiment the ARDS is viral ARDS or bacterial ARDS. In a more preferred embodiment the viral ARDS is COVID-19 ARDS.

Administration Regimen

In a preferred embodiment the inhibitor of C5a activity or the inhibitor of IL-6 activity are for administration in a regime comprising an induction phase followed by a maintenance phase. Preferably, the inhibitor of C5a activity is administered in the induction phase and the maintenance phase and the inhibitor of IL-6 activity is administered:
  (I) within 0-30 days, preferably within 0-15 days, more preferably within 0-7 days, most preferably within 0-1 days, prior to the induction phase,
  (II) during the induction phase, and/or
  (III) during the maintenance phase.

In a preferred embodiment, an additional second dose of the inhibitor of IL-6 activity is administered according to (I), (II) or (III).

In a preferred embodiment, the inhibitor of C5a activity is administered in the induction phase and the maintenance phase and the inhibitor of IL-6 activity is administered within 1 to 4 weeks, preferably within 1-2 weeks, more preferably within 1 week, prior to the induction phase.

In a preferred embodiment, the inhibitor of C5a activity is administered in the induction phase and the maintenance phase and the inhibitor of IL-6 activity is administered 1 to 14 days, preferable 1 to 7 days, prior to the induction phase.

In a preferred embodiment, the inhibitor of C5a activity is administered in the induction phase and the maintenance phase and the inhibitor of IL-6 activity is administered during the induction phase.

In a preferred embodiment, the inhibitor of C5a activity is administered in the induction phase and the maintenance phase and the inhibitor of IL-6 activity is administered during the maintenance phase.

In a preferred embodiment, the inhibitor of C5a activity is administered before the inhibitor of IL-6 activity In a preferred embodiment the induction phase has a duration of 1 to 10 days, preferably 2 to 8 days, more preferably 8 days.

In a preferred embodiment during the induction phase 1 to 8 doses, preferably 2 to 6 doses, more preferably 3 to 5 doses, most preferably 4 doses, of the inhibitor of C5a activity (preferably vilobelimab, INab708 or IFX-2, more preferably vilobelimab) are administered.

In a preferred embodiment, each dose administered in the induction phase comprises 200-1600 mg, preferably 400-1200 mg, more preferably 600-1000 mg, most preferably 800 mg, of the inhibitor of C5a activity (preferably vilobelimab, INab708 or IFX-2, more preferably vilobelimab).

In a preferred embodiment the inhibitor of C5a activity (preferably vilobelimab, INab708 or IFX-2, more preferably vilobelimab) is administered by intravenous infusion or injection, preferably infusion.

In a preferred embodiment the maintenance phase has a duration of 1 to 4 weeks, preferably 2-3 weeks, most preferably 2 weeks.

In a preferred embodiment during the maintenance phase, the inhibitor of C5a activity (preferably vilobelimab, INab708 or IFX-2, more preferably vilobelimab) is administered every 1 to 4 weeks, preferably 1 to 2 weeks, more preferably every week.

In a preferred embodiment, each dose administered in the maintenance phase comprises 200-1600 mg, preferably 400-1200 mg, more preferably 600-1000 mg, most preferably 800 mg, of the inhibitor of C5a activity (preferably vilobelimab, INab708 or IFX-2, more preferably vilobelimab).

In a preferred embodiment, the inhibitor of C5a activity and the inhibitor of IL-6 activity are used in an administration regimen, wherein
  (i) the induction phase comprises or essentially consists of a period of 1 to 10 days, preferably 2 to 8 days, more preferably 7-8 days, wherein 1-8 doses, preferably 2-4 doses, comprising each 200-1600 mg, preferably 400-1200 mg of said inhibitor of C5a activity (preferably vilobelimab, INab708 or IFX-2, more preferably vilobelimab), are administered; and
  (ii) the maintenance phase comprises or essentially consists of a period of at least 1 week, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week.

In a preferred embodiment, the inhibitor of C5a activity (preferably vilobelimab, INab708 or IFX-2, more preferably vilobelimab) is administered within the induction and the maintenance phase at a total maximum of 4 to 12 doses, preferably 6 to 10 doses, more preferably 6 to 8 doses, most preferably 6 doses.

In a preferred embodiment, the inhibitor of C5a activity and the inhibitor of IL-6 activity are used in an administration regimen, wherein
  (i) the induction phase essentially consists of a period of 8 days, wherein 4 doses comprising each 800 mg of the inhibitor of C5a activity (preferably vilobelimab, INab708 or IFX-2, more preferably vilobelimab), are administered (preferably on days 1, 2, 4 and 8); and
  (ii) the maintenance phase essentially consists of a period of 2 weeks, wherein a dose, comprising 800 mg of the inhibitor of C5a activity (preferably vilobelimab, INab708 or IFX-2, more preferably vilobelimab), is administered every 1 week (preferably on day 15 and 22 of the treatment).

In a preferred embodiment, the inhibitor of IL-6 activity (preferably tocilizumab) is administered at a dose of 200-1600 mg per dose, preferably 400-1200 mg, more preferably 600-1000 mg, most preferably 800 mg.

In a preferred embodiment, the inhibitor of IL-6 activity (preferably tocilizumab) is administered at a dose of 2 mg/kg to 12 mg/kg, preferably 3 mg/kg to 10 mg/kg, more preferably 4 mg/kg to 8 mg/kg.

In a preferred embodiment, the inhibitor of IL-6 activity (preferably tocilizumab) is administered at a weight dependent dose of 8 mg/kg for patients at or above 30 kg weight or 12 mg/kg for patients of less than 30 kg weight.

In a preferred embodiment, the inhibitor of IL-6 activity (preferably tocilizumab) is administered at a maximum dose of 800 mg per administration.

In a preferred embodiment, the inhibitor of IL-6 activity (preferably tocilizumab) is administered in 1 to 4 doses, preferably 1-2 doses.

In a preferred embodiment, the inhibitor of IL-6 activity (preferably tocilizumab) is administered as a single dose.

In a preferred embodiment, the inhibitor of IL-6 activity (preferably tocilizumab) is administered as a first and second dose. A second dose is in particular beneficial if clinical signs or symptoms do not improve after the first dose. Preferably, the additional dose is at administered at least 8 hours after the first dose.

In a preferred embodiment, each further dose of the inhibitor of IL-6 activity (preferably tocilizumab) is administered at least 8 hours after the previous administration.

In a preferred embodiment, an additional dose of the inhibitor of IL-6 activity (preferably tocilizumab) is administered 8-24 hours after the first dose.

In a preferred embodiment, the inhibitor of IL-6 activity (preferably tocilizumab) is administered every 1 to 4 weeks, preferably every 1 to 2 weeks, preferably weekly.

In a preferred embodiment, the inhibitor of IL-6 activity (preferably tocilizumab) is administered by intravenous infusion or injection, preferably infusion.

In a preferred embodiment, each dose of the inhibitor of IL-6 activity (preferably tocilizumab) is administered prior to the induction phase.

In a preferred embodiment, the inhibitor of IL-6 activity (preferably tocilizumab) is administered as 1-2 doses, preferably single dose, prior (preferably 1-2 weeks prior, more preferably within 1 week prior) to the induction phase.

In a preferred embodiment, the inhibitor of IL-6 activity (preferably tocilizumab) is administered within the induction phase.

In a preferred embodiment, the inhibitor of IL-6 activity (preferably tocilizumab) is administered in more than a single dose, wherein at least one dose is administered prior to the induction phase and at least one dose is administered in the induction phase and/or maintenance phase.

In a preferred embodiment, the inhibitor of IL-6 activity (preferably tocilizumab) is administered in more than a single dose, wherein at least one dose is administered prior to the induction phase and at least one dose is administered in the induction phase.

In a preferred embodiment, the inhibitor of IL-6 activity (preferably tocilizumab) is administered in more than a single dose, wherein at least one dose is administered in the induction phase and at least one dose is administered in the maintenance phase.

In a preferred embodiment, the inhibitor of C5a activity and the inhibitor of IL-6 activity are used in an administration regimen, wherein
  (i) 1 or 2 doses (preferably single dose) of the inhibitor of IL-6 activity (preferably tocilizumab) is administered within 0 to 14 days prior and/or after the start of the induction phase (preferably within 0 to 7 days (i.e. prior or after) of the start of the induction phase, more preferably within 24 hours (i.e. prior or after) of the start of the induction phase), preferably the inhibitor of IL-6 activity (preferably tocilizumab) is administered at a weight dependent dose of 8 mg/kg for patients at or above 30 kg weight or 12 mg/kg for patients of less than 30 kg weight;
  (ii) the induction phase comprises or essentially consists of a period of 1 to 10 days, preferably 2 to 8 days more preferably 7-8 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered; and
  (iii) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week.

In a preferred embodiment, the inhibitor of C5a activity and the inhibitor of IL-6 activity are used in an administration regimen, wherein
  (i) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
  (ii) 1 or 2 doses (preferably single dose) of the inhibitor of IL-6 activity (preferably tocilizumab) is administered within the induction phase; and
  (iii) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week.

In a preferred embodiment, the inhibitor of C5a activity and the inhibitor of IL-6 activity are used in an administration regimen, wherein
  (i) 1 or 2 doses (preferably single dose) of the inhibitor of IL-6 activity (preferably tocilizumab) is administered 1-2 weeks (preferably within 1 week of start of induction phase) prior to the induction phase;
(ii) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
(iii) 1 or 2 doses (preferably single dose) of the inhibitor of IL-6 activity (preferably tocilizumab) is administered within the induction phase; and
(iv) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week.

In a preferred embodiment, the inhibitor of C5a activity and the inhibitor of IL-6 activity are used in an administration regimen, wherein
(i) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
(ii) 1 or 2 doses (preferably single dose) of the inhibitor of IL-6 activity (preferably tocilizumab) is administered within the induction phase;
(iii) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week; and
(iv) 1 or 2 doses (preferably single dose) of the inhibitor of IL-6 activity (preferably tocilizumab) is administered within the maintenance phase.

In a preferred embodiment, the inhibitor of C5a activity and the inhibitor of IL-6 activity are used in an administration regimen, wherein
(i) 1 or 2 doses (preferably single dose) of the inhibitor of IL-6 activity (preferably tocilizumab) is administered within 0 to 14 days prior and/or after the start of the induction phase (preferably within 0 to 7 days (i.e. prior or after) of the start of the induction phase);
(ii) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
(iii) 1 or 2 doses (preferably single dose) of the inhibitor of IL-6 activity (preferably tocilizumab) is administered within the induction phase;
(iv) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week; and
(v) 1 or 2 doses (preferably single dose) of the inhibitor of IL-6 activity (preferably tocilizumab) is administered within the maintenance phase.

In a preferred embodiment, the inhibitor of C5a activity and the inhibitor of IL-6 activity are used in an administration regimen, wherein
(i) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
(ii) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week; and
(iii) 1 or 2 doses (preferably single dose) of the inhibitor of IL-6 activity (preferably tocilizumab) is administered within the maintenance phase.

In a preferred embodiment, the inhibitor of C5a activity and the inhibitor of IL-6 activity are used in an administration regimen, wherein
(i) 1 or 2 doses (preferably single dose) of the inhibitor of IL-6 activity (preferably tocilizumab) is administered within 0 to 14 days prior and/or after the start of the induction phase (preferably within 0 to 7 days (i.e. prior or after) of the start of the induction phase);
(ii) the induction phase comprises or essentially consists of a period of 1 to 10 days, preferably 2 to 5 days, wherein 1-8 doses, preferably 2-4 doses, comprising each 200-1600 mg, preferably 400-1200 mg of the inhibitor of C5a activity (preferably vilobelimab, INab708 or IFX-2, more preferably vilobelimab), are administered;
(iii) the maintenance phase comprises or essentially consists of a period of at least 2 weeks, preferably 2-4 weeks, wherein a dose, comprising 200-1600 mg, preferably 400-1200 mg of said inhibitor of C5a activity (preferably vilobelimab, INab708 or IFX-2, more preferably vilobelimab), is administered every 1-4 weeks, preferably every week; and
(iv) 1 or 2 doses (preferably single dose) of the inhibitor of IL-6 activity (preferably tocilizumab) is administered within the maintenance phase.

In a preferred embodiment, the inhibitor of C5a activity and the inhibitor of IL-6 activity are used in an administration regimen, wherein
(i) 1 dose of the inhibitor of IL-6 activity (preferably tocilizumab) is administered within 24 hours (i.e. prior or after) of the first administration of the inhibitor of C5a activity (preferably vilobelimab); optionally a second dose of the inhibitor of IL-6 activity (preferably tocilizumab) is administered, preferably after at least 8 hours of the first dose of the inhibitor of IL-6 activity; wherein the inhibitor of IL-6 activity (preferably tocilizumab) is administered at a weight dependent dose of 8 mg/kg for patients at or above 30 kg weight or 12 mg/kg for patients of less than 30 kg weight;
(ii) the inhibitor of C5a activity (preferably vilobelimab) is administered on day 1, day 2, day 4, day 8, day 15 and day 22, wherein the inhibitor of C5a activity (preferably vilobelimab) is administered at a dose of 800 mg.

Group of Patients

In a preferred embodiment the inhibitor of C5a activity or the inhibitor of IL-6 activity are for use in treating patients that are on invasive mechanical ventilation, preferably not more than 48 h post intubation upon first administration of the inhibitor of C5a activity.

In a preferred embodiment the inhibitor of C5a activity or the inhibitor of IL-6 activity are for use in treating patients that have a $PaO_2/FiO_2$ ratio of between 50 and 300, preferably between 60 and 200.

The ratio of partial pressure of oxygen in arterial blood ($PaO_2$) to the fraction of inspiratory oxygen concentration ($FiO_2$) is a clinical indicator of hypoxaemia. $PaO_2/FiO_2$ ratio is used inter alia to classify severity of acute respiratory distress syndrome (ARDS). In a preferred embodiment the following classification of ARDS severity is used: mild ($PaO_2/FiO_2$ ratio 200-300), moderate ($PaO_2/FiO_2$ ratio 100-200) and severe ($PaO_2/FiO_2$ ratio<100).

In a preferred embodiment the inhibitor of C5a activity or the inhibitor of IL-6 activity are for use in treating patients with mild to severe (preferably moderate to severe) ARDS.

Kit of Parts

In a third aspect, the present invention provides a kit of parts comprising an inhibitor of C5a activity (preferably vilobelimab) and an inhibitor of IL-6 activity (preferably tocilizumab). Preferably, the kit is further comprising instructions for the use of the inhibitor of C5a activity (preferably vilobelimab) and the inhibitor of IL-6 activity (preferably tocilizumab) and/or means for the application of the compounds.

In a preferred embodiment the kit of parts comprises the inhibitor of C5a activity (preferably vilobelimab) in a dosage form comprising 100-2000 mg, 200-1500 mg, 400-1200 mg, preferably 600-1000 mg, more preferably 800 mg of an inhibitor of C5a activity (preferably vilobelimab). Preferably wherein the dosage form is a lyophilized powder, or a liquid dosage form, preferably a solution for infusion or a solution for injection.

In a preferred embodiment the kit of parts comprises the inhibitor of IL-6 activity (preferably tocilizumab) in a dosage form comprising 100-2000 mg, 200-1500 mg, 400-1200 mg, preferably 600-1000 mg, more preferably 800 mg of an inhibitor of IL-6 activity (preferably tocilizumab). Preferably wherein the dosage form is a lyophilized powder, or a liquid dosage form, preferably a solution for infusion or a solution for injection.

Method of Treatment

In a further aspect of the invention a method for the treatment of patients with an infectious pneumonia and/or infectious acute respiratory distress syndrome (ARDS), wherein the method is comprising administering to the patient an effective amount of an inhibitor of C5a activity and an inhibitor of IL-6 activity. In a preferred embodiment the method comprises administering the inhibitor of IL-6 activity prior and/or concomitant with the inhibitor of C5a-activity.

In a third aspect, the present invention provides the use of an inhibitor of C5a activity and an inhibitor of IL-6 activity for the manufacturing of a medicament for the treatment of infectious pneumonia and/or infectious acute respiratory distress syndrome (ARDS).

EXAMPLES

The following Examples are provided for further illustration of the invention. The invention, however, is not limited thereto, and the following Examples merely show the practicability of the invention on the basis of the above description.

Example 1: Phase II/III Study Evaluating IFX-1 for the Treatment of COVID 19 Related Severe Pneumonia A) Rationale for the Study Neutrophil driven tissue and organ damage is known to play an important role in a wide array of acute inflammatory diseases. The mechanism leading to damage has been largely attributed to two mechanisms: 1) the release of granular enzymes and 2) the generation of so-called reactive oxygen species in which 02 radical formation elicits a damaging effect.

One of the strongest chemoattractant substances, which is also capable of inducing both mechanisms described above is the human complement split product C5a.

Earlier research by applicant has demonstrated that the anti-human C5a antibody IFX-1 could significantly reduce the neutrophil and macrophage infiltration in a model of viral (H7N9)-induced lung injury in monkeys (Sun et al. 2015). This was accompanied by a significantly reduced tissue damage in the lung of infected animals and also a significantly reduced viral replication when compared to mock-treated animals. The mechanism was then confirmed in a model of MERS-CoV-induced lung injury where similar findings were made by using an anti-C5a receptor antibody (Jiang et al. 2018) and in a model of SARS-CoV-induced lung injury by using complement C3 knockout mice (Gralinski et al. 2018). The latter study also provided evidence for a profound complement activation in SARS virus infections in animals. These studies all suggested a role of neutrophil driven lung damage, which was induced by generation of C5a in different viral-lung injury models, including SARS viruses.

Latest data from a collaborating research group in China demonstrated strongly and significantly elevated C5a levels in severely diseased COVID-19 patients when compared to mildly diseased patients (Gao et al. 2020; Carvelli et al. 2020) and revealed evidence for a strong complement pathway driven activation of C5a in this disease. In addition, data from the first two severely diseased COVID 19 patients treated with the IFX-1 cell line derived anti-C5a antibody BDB-1, which InflaRx licensed to a collaborator in China, demonstrated clinical improvement in oxygenation index, fever reduction, and laboratory parameter normalization including liver enzymes and lymphocyte counts.

From a clinical perspective, various papers have confirmed that COVID-19 infected non-surviving patients demonstrated lung failure with close to 100% (Zhou et al. 2020) and that, in contrast to surviving patients, non-survivors demonstrated elevated white blood cell counts and neutrophils above the normal range (Wang et al. 2020; Gong et al. 2020).

In summary, there is evidence that in COVID-19 patients who are severely affected, C5a activation occurs to a large extent and that neutrophil count elevation in blood is associated with bad outcome. These human data fit well to the scientific rationale developed in animal models of viral-induced lung injury that activated neutrophils attracted to the lung may cause viral-induced lung damage. First treatment attempts with the anti-C5a antibody technology developed by InflaRx (BDB-1) in severely affected COVID-19 patients provide further evidence for the scientific rationale.

The completed Phase II portion of the current trial was exploratory in nature and was not powered to show statistically significant differences in clinical endpoints. Relative change (%) from baseline to day 5 in the oxygenation index, chosen as the primary endpoint for Phase II, showed a large variability and dependency on patient positioning and intubation status which excluded this endpoint from being used in a confirmatory study. Phase III of the study is an adequately powered, placebo-controlled, double blinded phase evaluating standard of care (SOC)+IFX-1 versus SOC+placebo-to-match with 28-day all-cause mortality as the primary endpoint, an accepted regulatory primary endpoint for critical care studies.

At the time that Phase II of this study was initiated, there was no SOC established for this newly identified disease. The SOC to be utilized in Phase III of this study reflects the current understanding of the SOC for hospitalized patients with COVID-19, which includes venous thromboembolism (VTE) prophylaxis at a minimum, and may include other international and country-specific recommended treatments for COVID-19 per the locally adopted treatment recommendations.

Rationale for Dosage Regimen The aim for determining the dose and administration frequency for IFX-1 is to establish a pragmatic administration schedule for the COVID-19 patient population. IFX-1 dose and administration schedule was chosen based on prior pharmacokinetic (PK)/pharmacodynamic (PD) observations for IFX-1 trough values and blood C5a levels, dose-response assessment in Study IFX-1 in Hidradentis suppurativa, and the described unprecedented high C5a levels in patients with severe COVID-19 related pneumonia (Gao et al. 2020; Carvelli et al. 2020). In a population PK/PD modelling study for IFX 1 based on the data of the previous trials with IFX-1, a reduction in C5a concentration was found to be dependent on all measures of drug exposure, with increasing exposure predicting a greater reduction in C5a.

Based on the above data, the dosing schedule of IFX-1 for this study includes an additional dose of 800 mg IFX 1 at day 2 in the established fractionated loading dose scheme, that foresees administration of 800 mg at days 1, 4, and 8. This additional dose has been chosen due to the reported high C5a levels in COVID-19 patients (Gao et al. 2020). Therefore, the entire dosing scheme contains up to 6 IFX-1 doses of 800 mg at days 1, 2, 4, 8, 15, and 22 (or less until hospital discharge). This regimen had been employed in Phase II of this study, leading to a lower death rate and supporting efficacy signals without any new signals of unknown toxicities (Vlaar et al 2020).

B) Objectives of the Study
Primary Objectives
The primary objective of Phase III is:
To demonstrate the efficacy of IFX-1 to improve survival outcomes of severe COVID 19 pneumonia (confirmative)
Secondary Objectives
The secondary objectives of Phase III are:
To assess and define other parameters of efficacy
To assess the safety of IFX-1
C) Study Design
Overall Design
This is a pragmatic, adaptive, randomized, multicenter phase II/III study evaluating IFX-1 for the treatment of COVID 19 related severe pneumonia. Phase III is a double-blind, placebo-controlled, randomized phase evaluating SOC+IFX-1 (Arm A) and SOC+placebo-to-match (Arm B). The SOC includes VTE prophylaxis at a minimum, and may include other international and country-specific recommended treatments for COVID-19 per the locally adopted treatment recommendations.

Phase III of the study will randomize up to 400 patients with one interim analysis for stopping for futility. A total of 180 patients are planned to be randomized into Arm A and Arm B using a 1:1 allocation ratio for the first stage; based on results of the interim analysis, up to an additional 180 patients are planned to be randomized using the same allocation ratio for the second stage. Additional patients will be randomized under the following conditions:

For patients who were erroneously randomized (screening failures) and did not get IMP treatment.

For patients who were randomized but consent was withdrawn (either by the patient or patient representative) within the first 48 hours after randomization, irrespective of whether IMP was administered or not.

The primary statistical analysis will be based on all randomized patients except patients randomized in error who did not get IMP treatment.

In Phase III, patients will be treated with a maximum of 6 IV doses of IFX-1 800 mg (Arm A) or placebo (Arm B) at days 1, 2, 4, 8, 15, and 22, as long as the patient is still in the hospital (even if discharged from the ICU).

Patients will be assessed for quality of life using the EQ-5D.

Patients will be followed for survival and their clinical status assessed by the Glasgow Outcome Scale.

End of Treatment and Follow-Up

End of treatment (EOT) is defined as the last planned administration or discontinuation of IMP for other reasons.

The FUV is scheduled to occur 28 days (if patient has been discharged) and 60 days after the randomization date. The visit information obtained at a site visit or via telephone call (e.g., AEs, survival status, according to the SoA) should be recorded.

Discontinuation of study treatment does not represent withdrawal from the study.

End of Study

The end of study for the individual patient is defined as the date of the last contact of the follow up period (i.e., 60 days after randomization), date of death, date of consent withdrawal from study participation, or the date of last contact when patients are lost to follow-up, whatever occurs earliest.

The entire study will end when all patients have discontinued IFX 1 AND all patients ended the study as described above.

D) Study Population
Inclusion Criteria
Patients must meet all the following criteria at randomization to be enrolled into Phase III of the study:
1. At least 18 years of age or older
2. Patient on invasive mechanical ventilation (but not more than 48 h post intubation at time point of first IMP administration)
3. Patients with a $PaO_2/FiO_2$ ratio of <200 and >60 at randomization (one representative measurement within 6 h before randomization)
4. SARS-CoV-2 infection confirmation (tested positive in last 14 days before randomization with locally available test system)

Exclusion Criteria

Patients who fulfill any of the following criteria at randomization are not eligible to participate in Phase III of the study:
1. Intubated>48 h at time point of first IMP administration
2. Expected stop of invasive ventilation or expected extubation in the next 24 h without additional intervention according to judgment of the investigator
3. Known history of chronic dialysis OR received renal replacement therapy in past 14 days OR anticipated to receive renal replacement therapy within 24 h after randomization
4. Known history of progressed COPD as evidenced by use of daily maintenance treatment with long-acting bronchodilators or inhaled/oral corticosteroids for >2 months
5. Treatment of COVID-19 with investigational antibody treatment(s) which are not approved or not included in locally adopted treatment guidelines (e.g., WHO guidance, National Institutes of Health [NIH] COVID-19 treatment guidelines) for this indication in the past 7 days (Note: Antibody treatment[s] given within past 7 days for pre existing diseases, other than COVID-19, are allowed.)
6. At time point of randomization, treatment of COVID 19 with investigational treatments which are not approved or not included in locally adopted treatment guidelines for this indication (e.g., WHO guidance, NIH COVID-19 treatment guidelines), including SARS CoV-2 multiplication inhibitor(s) or immunomodulator(s). (Note: If a locally adopted treatment guideline recommends drugs such as remdesivir, dexamethasone, or anticoagulation, this would be allowed. Adopted guidelines and updates must be documented at study initiation and throughout the conduct of the study.)
7. Received cytokine adsorption therapy in past 3 days
8. Known hypersensitivity to IFX-1 or any other ingredient of the study medication
9. Serum or urine pregnancy test positive before randomization (required for women of childbearing potential)
10. Received organ or bone marrow transplantation in past 3 months
11. Known cardio-pulmonary mechanical resuscitation in past 14 days
12. Patient moribund or expected to die in next 24 h according to the judgment of the investigator
13. Known to have received anti-cancer therapy for hemato-oncological disease in past 4 weeks OR known to have active malignant disease at time point of randomization
14. Known severe congestive heart failure (corresponding to e.g. NYHA Class III-IV, left ventricular ejection fraction<40%; see Appendix 8)
15. Known history of chronic liver disease (Child-Pugh B or C; see Appendix 11)
16. Participating in or has participated in other investigational interventional studies (drug or device) within the last 7 days before randomization Screen Failures Screening failures are defined as patients who do not meet the criteria for participation in this study and thus, are either not randomized/assigned to IMP or randomized in error and do/did not receive IMP. Screen failure data for not randomized patients will not be recorded in the eCRF, for those patients who are randomized in error, screen failure data are to be recorded in the eCRF.

Rescreening does not apply to this study.

E) Study Intervention

Investigational Medicinal Product (IMP)

The IMP is defined as the investigational treatment IFX-1 and Placebo-to-match (Placebo) that is intended to be administered to a study patient according to the study protocol.

IFX-1 concentrate solution for infusion will be supplied in 20 mL glass vials at a concentration of 10 mg/mL (200 mg per vial) for reconstitution and IV administration. Apart from IFX 1, the solution will contain sodium chloride, sodium phosphate, and polysorbate 80.

Placebo concentrate solution for infusion will be supplied in 20 mL glass vials for reconstitution and IV administration. The solution will contain sodium chloride, sodium phosphate, and polysorbate 80.

Administration and Dosage

For Phase III, patients are randomized to either receive SOC+IFX-1 in treatment Arm A or SOC+Placebo in treatment Arm B. The first dose of IFX-1 or Placebo is administered at Day 1. SOC may start at any time according to their administration schedule.

Close observation of IFX-1 or Placebo infusion(s) is required for monitoring of potential infusion reactions. Appropriate treatment for potential infusion reactions must be available during this time.

Patients will be treated with a maximum of 6 IV doses of IFX-1 800 mg (Arm A) or placebo (Arm B) administered as a 30-60-minute IV infusion. The 6 treatments are at days 1, 2, 4, 8, 15, and 22 as long as the patient is still in the hospital, even if discharged from ICU. IMP administrations for Phase III are detailed in FIG. 1.

Prior and Concomitant Medication/Treatments

In Phase III of the study, in addition to the IMP, all patients will receive SOC for treatment of COVID-19, which includes VTE prophylaxis with anticoagulants at a minimum. Other international or country-specific recommended treatments for COVID-19 per the locally adopted treatment recommendations (including but not limited to corticosteroids, remdesivir, and other local SOC) are allowed as concomitant medications. SOC treatment start and stop is not defined by the protocol and can start at any time. SOC treatment will be given according to investigator's discretion.

Reportable medications or vaccinations that the patient is receiving within 7 days prior to randomization and up to 30 days after the last dose of study treatment should be recorded along with:
Reason for use
Dates of administration including start and end dates F) Study Assessments and Procedures Baseline Assessments (Screening)

The following procedures will be performed to assess baseline characteristics during screening evaluations and before randomization and IMP administration:
Check inclusion and exclusion criteria
Documentation of demographic details (age, gender, race, and ethnicity), medical and COVID-19 history. Race information is required for eGFR calculation using the CKD-EPI equation
8-point ordinal scale assessment and oxygenation index ($PaO_2/FiO_2$; one representative measurement within 6 h before randomization)
Documentation of concomitant disease and prior medications Baseline safety assessment (height, weight, physical exam, AEs, ECG, urine analysis, pregnancy test, and clinical safety laboratory [including creatinine assessment]))

Prior and Concomitant Medications and Procedures

All procedures performed or medications administered within 7 days before randomization should be recorded as prior procedures and prior medication with generic name, start date, stop date, and indication for treatment.

Reporting of prior and concomitant medications will follow special considerations for conditions in the ICU. A complete record of all prior and concomitant medications (but excluding nutritional and volume therapy, electrolyte support, vitamins, non-steroidal anti-inflammatory drugs (NSAIDs), and supportive therapies such as artificial tears, ointments, stool softeners/laxatives, etc.) will be maintained in the eCRF for each participant, beginning 7 days before randomization and continuing up to 30 days after the last dose of study treatment).

In addition, a complete record of all steroid and antibiotic therapy, as well as any therapy (medications, specific treatments, etc.) associated with or used in the assessment or treatment of an AE will be documented for the duration of the study.

The following information must be recorded in the eCRF for each reportable concomitant medication: generic name, route of administration, start date, stop date, and indication G) Adverse Events Definition of Adverse Events (AE):

An AE is any untoward medical occurrence in a subject administered an IMP; an AE does not necessarily have to have a causal relationship with this treatment.

AEs encompass any unfavorable and unintended sign (including an abnormal laboratory finding), symptom, or disease that arises or worsens after the inclusion of the subject into the study.

H) Statistical Considerations

Determination of Sample Size

A total of 180 patients (90 per arm) are planned to be randomized in Stage 1 and up to 180 patients (90 per arm) in Stage 2. For patients randomized in error (screening failures) and patients for whom consent is withdrawn within 48 hours after randomization, additional patients will be randomized. This results in 90% overall power to show efficacy in the final efficacy analysis. The power calculation is based on an overall 2.5% one-sided alpha and an assumed 30% 28-day mortality under Placebo and 15% 28-day mortality under IFX-1 treatment.

Analysis Sets

Full analysis set (FAS): The primary statistical analysis will be based on all randomized patients except patients randomized in error (reason for early termination documented as "Randomized by mistake" in the eCRF) who did not get IMP treatment.

Safety analysis set (SAF): Safety analyses will be based on all patients who received at least one infusion of IMP, and patients will be analyzed according to the treatment they actually received.

Statistical Analyses

Primary Efficacy Analysis

The primary analysis will be performed based on the FAS.

The primary efficacy variable is 28-day mortality (proportion of patients deceased until day 28). The primary statistical hypotheses to be tested are:

$H_0$: HR=1
versus
$H_1$: HR>1 where HR is the hazard ratio derived from the beta coefficient of the primary statistical analysis Cox regression model comparing the SOC+Placebo treatment arm (Arm B) with the SOC+IFX-1 treatment arm (Arm A).

A total of 180 patients are planned to be randomized to Arm A and Arm B using a 1:1 allocation ratio for the first stage. The interim analysis is performed after 180 patients, not counting patients being randomized in error, have been followed-up until day 28 (or died before). In case the interim analysis does not result in an early stop for futility, 180 additional patients are planned to be randomized in a ratio of 1:1 to Arm A and B. The planned maximum number of patients in the study is 360. Depending on the number of patients meeting criteria for additional randomization, more patients will be randomized but not more than 400.

The primary statistical analysis of IFX-1+SOC compared to SOC alone will make use of a one-sided alpha level of 2.5% and will test for superiority (lower mortality among IFX-1 treated patients). The primary statistical analysis will be based on a Cox proportional hazards regression model with outcome 28-day all-cause mortality as a censored time-to-event variable and explanatory variables treatment arm (Arm B versus Arm A) and age. The primary statistical analysis will be based on all randomized patients except patients randomized in error (reason for early termination documented as "Randomized by mistake" in the eCRF) who did not get IMP treatment. For the primary analysis, all-cause mortality will be censored at day 28 for subjects who died after day 28 or who have more than 28 days follow-up alive.

The z-statistic for the interim and final analysis will be calculated as the proportion of the beta coefficient for the treatment arm effect and its standard error from the Cox proportional hazards regression model. The study will be stopped for futility if the z-statistic for the first stage is 0 or lower.

Secondary Efficacy Analysis

The secondary efficacy analyses will be performed based on the FAS.

The first secondary efficacy endpoint will only be addressed with statistical hypothesis tests if the primary endpoint is statistically significant using the full overall 2.5% one-sided alpha. If the first secondary endpoint is also statistically significant, the full 2.5% one-sided alpha will be passed to the 4 remaining secondary endpoints. Multiplicity in the secondary endpoints will be addressed with the fallback method. 60-day mortality will be analyzed similar to 28-day mortality and the other secondary endpoints will be evaluated using a logistic regression model with the explanatory variables randomized treatment arm (Arm B versus Arm A) and age for:

1. 60-day all-cause mortality
2. Proportion of patients with an improvement in the provided 8-point ordinal scale at day 15 (at least one score point lower than at randomization)
3. Proportion of patients with an improvement in the provided 8-point ordinal scale at day 28 (at least one score point lower than at randomization)
4. Proportion of patients developing acute kidney failure (eGFR<15 mL/min/1.73 $m^2$) during ICU stay and at day 28
5. Proportion of patients free of any renal replacement therapy within 28 days upon randomization The ordering of the secondary endpoints 2 to 5 for hypothesis testing will be as in above mentioned list. The full 2.5% one-sided alpha for the fallback method will be attributed to the 4 secondary endpoints in the following way 2%, 0.2%, 0.2%, and 0.1%. If the preceding hypothesis test is not significant, subsequent tests will be performed at the aforementioned alpha level. If tests are significant, the alpha is added to the subsequent hypothesis test (e.g., if the primary hypothesis test is significant and secondary endpoints 1-4 are all significant, the fifth secondary endpoint will be tested at an alpha of 2.5%; if the fourth secondary endpoint is not significant, the fifth secondary endpoint will be tested at an alpha of 0.1%).

The primary endpoint as well as all secondary endpoints will also be evaluated as censored time to event variables by Kaplan-Meier type methods. Kaplan-Meier analyses will be performed comparing the two treatment arms overall and within the following stratifications:

Stratification by site
Stratification by country
Stratification by sex
Stratification by age
Stratification by comorbidities
Stratification by standard or care.

Other Efficacy Analyses
Time to First Extubation

Time to first extubation will be analyzed as a censored time to event variable. Withdrawing early from the study will lead to the patient being right-censored at the date of withdrawal provided that the reason is not an outcome of interest (extubation or death). In order to adequately account for competing outcomes as well as potential right-censoring due to varying follow-up times, the outcome will be non-parametrically analyzed using Aalen-Johansen-type estimation based on a competing risks model with two absorbing states (event 1: all-cause death; event 2: extubation). Adjustment for age will be realized by regression modeling accounting for competing risks.

Patients Alive and Free of Respiratory Failure

Patients achieving 8-point ordinal scale score 3 or below (patients alive and free of respiratory failure) at day 15 and day 28 are defined as alive and free of respiratory failure at the respective study day. The corresponding endpoint will be analyzed using logistic regression with explanatory variables age and treatment group.

Glasgow Outcome Scale

Glasgow Outcome Scale assessed at study day 60 will be analyzed via ordinal logistic regression with explanatory variables treatment arm (Arm B versus Arm A) and age.

Quality of Life

Quality of life will be assessed by EQ-5D at study day 60. The visual analogue scale as well as an index value based on the 5 health states (cross-walk index value using the United States value set) will be analyzed by an ANCOVA model with explanatory variables treatment arm (Arm B versus Arm A), age, and sex (male versus female).

Interim Analysis

The interim analysis is performed after the first 180 patients, not counting patients being randomized in error, in Stage 1 have been followed-up until day 28 (or died before). The study will be stopped for futility if the z-statistic of the primary efficacy analysis is 0 or lower. If the study is not stopped for futility, another up to 180 patients will be randomized in Stage 2. Depending on the number of patients meeting criteria for additional randomization, more than 360 patients will be randomized but not more than a total of 400.

Example 2: Patients Receiving Combined Treatment of IFX-1 and Tocilizumab in Phase III Study Evaluating IFX-1 for the Treatment of COVID 19 Related Severe Pneumonia A) Prior or Concomitant Use of Tocilizumab Some patients enrolled in the phase III trial outlined in example 1 above where also receiving the anti-IL-6 receptor antibody Tocilizumab, which had received an emergency use authorization by the FDA and EMA for the treatment of severe COVID-19.

Unexpectedly, patients receiving both medications, i.e. IFX-1 (vilobelimab) and tocilizumab, exhibited a highly significant reduction of all-cause mortality as compared to placebo treatment as well as single use of vilobelimab or tocilizumab.

This significant reduction was observed in patients receiving tocilizumab prior to first administration of vilobelimab (i.e. tocilizumab baseline use) as well as concomitant use of both compounds.

For the purpose of the present application the following definitions of baseline use and concomitant use will be used Baseline use of tocilizumab is defined as receiving at least one dose of tocilizumab between study day −7 and study day 1.

Prior use of tocilizumab is defined as receiving at least one dose of tocilizumab before day-7 (i.e. prior to baseline use)

concomitant use: Medications will be counted as concomitant either if they have an end date/time later than the timestamp of randomization or if "ongoing" is ticked on the respective eCRF page.

If the end date/time is completely missing and "ongoing" is not ticked, the previous medication will also be assumed to be concomitant. Incomplete start/end dates will not be imputed. If the incomplete date does not allow clear categorization as previous or concomitant medication, the medication will be counted as concomitant.

For the Cox proportional hazard models and Kaplan-Meier curves reported herein tocilizumab use is either classified as 'baseline usage of Tocilizumab' or 'any usage of Tocilizumab', whereas the later encompasses prior use, baseline use and concomitant use.

B) Effect of Combined Treatment with an Inhibitor of C5a Activity and an Inhibitor of IL-6 Activity The primary statistical analysis is based on a Cox proportional hazards regression model with outcome 28-day and 60-day all-cause mortality as a censored time-to-event variable and explanatory variables treatment arm (Arm B (i.e. placebo+SOC) versus Arm A (i.e. vilobelimab+SOC) and age. This statistical analysis was made with patients receiving Tocilizumab (baseline use or any use) in Arm A and or Arm B.

Of note, a hazard ratio (HR) above 1 indicates a covariate that is positively associated with the event probability, and thus negatively associated with the length of survival. In summary, HR=1: No effect, HR<1: Reduction in the hazard and HR>1: Increase in Hazard. Therefore a covariate with a hazard ratio>1 is a bad prognostic factor and a covariate with a hazard ratio<1 is called good prognostic factor.

Combined Treatment Vilobelimab and Tocilizumab (any Usage)

As shown in Table 2 below, the 28-day all-cause-mortality for patients receiving vilobelimab and tocilizumab (any usage) is significantly reduced as compared to the placebo group (i.e. tocilizumab any usage) (p=0.0098, HR: 0.140). In other words, the combined treatment of vilobelimab and tocilizumab (any usage) is significantly more effective in reducing all cause mortality as compared to tocilizumab alone. All treatment group received in addition to the indicated treatment also standard of care (SOC).

TABLE 2

Cox proportional hazard model for 28-day all-cause mortality for patients with any usage of Tocilizumab – FAS; (number of patients in analysis set/model: 61/61)

| Parameter | HR | 95% CI* HR | p-value | Beta coefficient | Standard error | Z statistic |
|---|---|---|---|---|---|---|
| Treatment (Vilo + SOC) | 0.140 | [0.031; 0.622] | 0.0098 | −1.96842 | 0.76176 | −2.584 |
| Age | 1.064 | [1.009; 1.123] | 0.0229 | 0.06239 | 0.02742 | |

*Wald-type confidence intervals; HR = Hazard Ratio; FAS = Full analysis set; SOC = Standard of care; Vilo = Vilobelimab The same significant reduction is observed for 60-day all-cause mortality as shown in Table 3 below. The treatment group receiving vilobelimab and tocilizumab (any usage) had a significantly reduced all-cause mortality as compared with the placebo group (i.e. tocilizumab any usage) (p=0.0187; HR: 0.296).

TABLE 3

Cox proportional hazard model for 60-day all-cause mortality for patients with any usage of Tocilizumab-FAS; (number of patients in analysis set/model: 61/61)

| Parameter | HR | 95% CI* HR | p-value | Beta coefficient | Standard error |
|---|---|---|---|---|---|
| Treatment (Vilo + SOC) | 0.296 | [0.107; 0.816] | 0.0187 | −1.21864 | 0.51828 |
| Age | 1.057 | [1.010; 1.106] | 0.0175 | 0.05537 | 0.02330 |

*Wald-type confidence intervals; HR = Hazard Ratio; FAS = Full analysis set; SOC = Standard of care; Vilo = Vilobelimab Combined Treatment Vilobelimab and Tocilizumab (Baseline Usage)

A similar effect was observed for baseline usage of Tocilizumab (defined as receiving at least one dose of tocilizumab between study day −7 and study day 1).

The 28-day all-cause mortality was dramatically reduced if the patients received baseline usage of Tocilizumab in combination with vilobelimab as indicated by the hazard ratio of 0.0.073 (p=0.012; see Table 4 below).

TABLE 4

Cox proportional hazard model for 28-day all-cause mortality for patients with baseline usage of Tocilizumab-FAS; (number of patients in analysis set/model: 60/60);

| Parameter | HR | 95% CI* HR | p-value | Beta coefficient | Standard error | Z statistic |
|---|---|---|---|---|---|---|
| Treatment (Vilo + SOC) | 0.073 | [0.010; 0.563] | 0.0120 | −2.61183 | 1.03942 | −2.5128 |
| Age | 1.067 | [1.009; 1.128] | 0.0238 | 0.06448 | 0.02853 | |

*Wald-type confidence intervals; HR = Hazard Ratio; FAS = Full analysis set; SOC = Standard of care; Vilo = Vilobelimab A similar effect was observed for 60-day all-cause mortality after Tocilizumab baseline usage. The all-cause mortality was dramatically reduced as indicated by the hazard ratio of 0.245 (p=0.0127; see Table 5 below).

TABLE 5

Cox proportional hazard model for 60-day all-cause mortality for patients with baseline usage of Tocilizumab-FAS; (number of patients in analysis set/model: 60/60)

| Parameter | HR | 95% CI* HR | p-value | Beta coefficient | Standard error |
|---|---|---|---|---|---|
| Treatment (Vilo + SOC) | 0.245 | [0.081; 0.741] | 0.0127 | −1.40676 | 0.56465 |
| Age | 1.058 | [1.010; 1.109] | 0.0183 | 0.05653 | 0.02396 |

*Wald-type confidence intervals; HR = Hazard Ratio; FAS = Full analysis set; SOC = Standard of care; Vilo = Vilobelimab Treatment with Vilobelimab without any Usage of Tocilizumab Patients treated with vilobelimab alone also had a reduced 28-day all-cause mortality as compared to placebo (no tocilizumab use). However, the effect, as indicated by the hazard ratio of 0.793, was much smaller than the combination of vilobelimab and tocilizumab (HR=0.140).

TABLE 6

Cox proportional hazard model for 28-day all-cause mortality for patients without any usage of Tocilizumab-FAS; (number of patients in analysis set/model: 307/307)

| Parameter | HR | 95% CI* HR | p-value | Beta coefficient | Standard error | Z statistic |
|---|---|---|---|---|---|---|
| Treatment (Vilo + SOC) | 0.793 | [0.550; 1.145] | 0.2157 | −0.231688 | 0.18713 | −1.2381 |
| Age | 1.024 | [1.010; 1.038] | 0.0010 | 0.02368 | 0.00718 | |

*Wald-type confidence intervals; HR = Hazard Ratio; FAS = Full analysis set; SOC = Standard of care; Vilo = Vilobelimab The same was observed for 60-day all-cause mortality. Here all-cause mortality was also reduced, but with a similar hazard ratio of 0.756 (see Table 7 below) as compared to the combination of vilobelimab and tocilizumab (HR=0.296).

TABLE 7

Cox proportional hazard model for 60-day all-cause mortality for patients without any usage of Tocilizumab-FAS; (number of patients in analysis set/model: 61/61)

| Parameter | HR | 95% CI* HR | p-value | Beta coefficient | Standard error |
|---|---|---|---|---|---|
| Treatment (Vilo + SOC) | 0.756 | [0.534; 1.071] | 0.1158 | −0.27956 | 0.17776 |
| Age | 1.029 | [1.015; 1.044] | <0.0001 | 0.02900 | 0.00695 |

*Wald-type confidence intervals; HR = Hazard Ratio; FAS = Full analysis set; SOC = Standard of care; Vilo = Vilobelimab Essentially the same result was achieved in the treatment group not receiving baseline usage of Tocilizumab. For the sake of clarity, these group of patients (i.e. no baseline use of Tocilizumab) did not receive any Tocilizumab administration (neither baseline nor any other use), but rather vilobelimab or placebo treatment. The all-cause mortality for 28-days and 60-days was reduced by vilobelimab treatment as indicated by the hazard ratios of 0.801 and 0.763 respectively (see Tables 8 and 9 below).

TABLE 8

Cox proportional hazard model for 28-day all-cause mortality for patients without baseline usage of Tocilizumab-FAS; (number of patients in analysis set/model: 308/308)

| Parameter | HR | 95% CI* HR | p-value | Beta coefficient | Standard error | Z statistic |
|---|---|---|---|---|---|---|
| Treatment (Vilo + SOC) | 0.801 | [0.556; 1.154] | 0.2343 | −0.22140 | 0.18617 | −1.1892 |
| Age | 1.024 | [1.010; 1.039] | 0.0009 | 0.02381 | 0.00717 | |

*Wald-type confidence intervals; HR = Hazard Ratio; FAS = Full analysis set; SOC = Standard of care; Vilo = Vilobelimab

TABLE 9

Cox proportional hazard model for 60-day all-cause mortality for patients without baseline usage of Tocilizumab-FAS; (number of patients in analysis set/model: 308/308)

| Parameter | HR | 95% CI* HR | p-value | Beta coefficient | Standard error |
|---|---|---|---|---|---|
| Treatment (Vilo + SOC) | 0.763 | [0.540; 1.080] | 0.1269 | −0.27003 | 0.17691 |
| Age | 1.030 | [1.016; 1.044] | <0.0001 | 0.02910 | 0.00694 |

*Wald-type confidence intervals; HR = Hazard Ratio; FAS = Full analysis set; SOC = Standard of care; Vilo = Vilobelimab Baseline Usage of Tocilizumab and Interaction with Vilobelimab Treatment Further Cox proportional hazard models as a censored time-to-event variable and explanatory variables treatment arm and age and baseline tocilizumab use flag and its interaction with study treatment were established.

In a first analysis the 28-day all-cause mortality with baseline tocilizumab was investigated. As indicated in table 10 below, treatment with vilobelimab alone (i.e. "Treatment (Vilo vs Placebo) for baseline tocilizumab use: no") had only a small effect on 28 day survival rate with a HR of 0.797. Likewise the baseline use of tocilizumab without vilobelimab ("Baseline Tocilizumab use (yes vs no) for Treatment: Placebo") had a minor effect on survival rate with a HR of 0.844.

In contrast the interaction of vilobelimab treatment with baseline use of tocilizumab ("Treatment (Vilo vs Placebo) for baseline tocilizumab use: yes") resulted in a robust effect on survival with a HR of only 0.073. Consistently, the same robust effect on survival was observed for baseline Tocilizumab use interaction with vilobelimab treatment with a HR of 0.077.

Taken together the combined treatment of vilobelimab and baseline tocilizumab resulted in a dramatic increase of survival whereas the treatment with vilobelimab or tocilizumab alone only had a minor effect.

TABLE 10

Cox proportional hazards regression model with outcome 28-day all-cause mortality as a censored time-to-event variable and explanatory variables treatment arm and age and baseline tocilizumab use flag and its interaction with study treatment-FAS. (number of patients in analysis set/model: 368/368)

| Parameter | HR | 95% CI* HR |
|---|---|---|
| Treatment (Vilo vs Placebo) for baseline tocilizumab use: no | 0.797 | [0.554; 1.148] |
| Treatment (Vilo vs Placebo) for baseline tocilizumab use: yes | 0.073 | [0.010; 0.559] |
| Baseline Tocilizumab use (yes vs no) for Treatment: Vilo | 0.077 | [0.011; 0.560] |
| Baseline Tocilizumab use (yes vs no) for Treatment: Placebo | 0.844 | [0.464; 1.538] |

*Wald-type confidence intervals; HR = Hazard Ratio; FAS = Full analysis set; SOC = Standard of care; Vilo = Vilobelimab As similar effect of the respective treatments was observed for 60-day all-cause mortality as summarized in Table 11 below.

| Parameter | HR | 95% CI* HR | p-value | Beta coefficient | Standard error | Z statistic |
|---|---|---|---|---|---|---|
| Treatment (Vilo + SOC) | | | 0.2233 | −0.22663 | 0.18610 | −1.2178 |
| Age | 1.027 | [1.013; 1.041] | 0.0002 | 0.02647 | 0.00699 | |
| Baseline use of Tocilizumab (yes/no) | | | 0.5801 | −0.16925 | 0.30596 | |
| Baseline use of Tocilizumab (yes/no) interaction with Treatment | | | 0.0234 | −2.38968 | 1.05446 | |

| Parameter | HR | 95% CI* HR | p-value | Beta coefficient | Standard error |
|---|---|---|---|---|---|
| Treatment (Vilo + SOC) | | | 0.1165 | −0.27759 | 0.17686 |
| Age | 1.032 | [1.019; 1.046] | <0.0001 | 0.03161 | 0.00669 |
| Baseline use of Tocilizumab (yes/no) | | | 0.5376 | −0.17595 | 0.28544 |
| Baseline use of Tocilizumab (yes/no) interaction with Treatment | | | 0.0596 | −1.11191 | 0.59024 |

TABLE 11

Cox proportional hazards regression model with outcome 60-day all-cause mortality as a censored time-to-event variable and explanatory variables treatment arm and age and baseline tocilizumab use flag and its interaction with study treatment-FAS. (number of patients in analysis set/model: 368/368)

| Parameter | HR | 95% CI* HR |
|---|---|---|
| Treatment (Vilo vs Placebo) for baseline tocilizumab use: no | 0.758 | [0.536; 1.071] |
| Treatment (Vilo vs Placebo) for baseline tocilizumab use: yes | 0.249 | [0.083; 0.751] |
| Baseline Tocilizumab use (yes vs no) for Treatment: Vilo | 0.276 | [0.100; 0.760] |
| Baseline Tocilizumab use (yes vs no) for Treatment: Placebo | 0.839 | [0.479; 1.467] |

*Wald-type confidence intervals; HR = Hazard Ratio; FAS = Full analysis set; SOC = Standard of care; Vilo = Vilobelimab Any Usage of Tocilizumab and Interaction with Vilobelimab Treatment The statistical analysis including interaction of the different treatments for any usage of Tocilizumab on 28-day all-cause mortality had a similar result as disclosed above for baseline usage of Tocilizumab (see Table 12 below). The treatment with only vilobelimab ("Treatment (Vilo vs Placebo) for any tocilizumab use: no had in this group of patient") had in this group of patients a minor effect as indicated by a HR of 0.789. Likewise treatment with only tocilizumab (any usage) ("Any Tocilizumab use (yes vs no) for Treatment: Placebo") had a minor effect as indicated by a HR of 0.844.

In contrast and consistent with the observation for baseline usage of Tocilizumab the interaction of vilobelimab treatment with baseline use of tocilizumab ("Treatment (Vilo vs Placebo) for any tocilizumab use: yes") resulted in a robust effect on survival with a HR of only 0.249. Consistently, the same robust effect on survival was observed for any Tocilizumab use interaction with vilobelimab treatment with a HR of 0.276.

| Parameter | HR | 95% CI* HR | p-value | Beta coefficient | Standard error | Z statistic |
|---|---|---|---|---|---|---|
| Treatment (Vilo + SOC) | | | 0.2044 | −0.23742 | 0.18707 | −1.2691 |
| Age | 1.027 | [1.013; 1.041] | 0.0002 | 0.02644 | 0.00698 | |
| Any use of Tocilizumab (yes/no) | | | 0.5803 | −0.16916 | 0.30596 | |
| Any use of Tocilizumab (yes/no) interaction with Treatment | | | 0.0281 | −1.71718 | 0.78217 | |

TABLE 12

Cox proportional hazards regression model with outcome 28-day all-cause mortality as a censored time-to-event variable and explanatory variables treatment arm and age and any tocilizumab use flag and its interaction with study treatment-FAS. (number of patients in analysis set/model: 368/368)

| Parameter | HR | 95% CI* HR |
|---|---|---|
| Treatment (Vilo vs Placebo) for any tocilizumab use: no | 0.789 | [0.547; 1.138] |
| Treatment (Vilo vs Placebo) for any tocilizumab use: yes | 0.142 | [0.032; 0.627] |
| Any Tocilizumab use (yes vs no) for Treatment: Vilo | 0.152 | [0.037; 0.622] |
| Any Tocilizumab use (yes vs no) for Treatment: Placebo | 0.844 | [0.464; 1.538] |

*Wald-type confidence intervals; HR = Hazard Ratio; FAS = Full analysis set; SOC = Standard of care; Vilo = Vilobelimab A virtually identical result was observed for 60-day all-cause mortality as disclosed in Table 13 below.

| Parameter | HR | 95% CI* HR | p-value | Beta coefficient | Standard error |
|---|---|---|---|---|---|
| Treatment (Vilo + SOC) | | | 0.1055 | −0.28765 | 0.17772 |
| Age | 1.032 | [1.019; 1.046] | <0.0001 | 0.03156 | 0.00668 |
| Any use of Tocilizumab (yes/no) | | | 0.5381 | −0.17574 | 0.28544 |
| Any use of Tocilizumab (yes/no) interaction with Treatment | | | 0.0971 | −0.90677 | 0.54651 |

TABLE 13

Cox proportional hazards regression model with outcome 60-day all-cause mortality as a censored time-to-event variable and explanatory variables treatment arm and age and any tocilizumab use flag and its interaction with study treatment-FAS. (number of patients in analysis set/model: 368/368)

| Parameter | HR | 95% CI* HR |
|---|---|---|
| Treatment (Vilo vs Placebo) for any tocilizumab use: no | 0.750 | [0.529; 1.063] |
| Treatment (Vilo vs Placebo) for any tocilizumab use: yes | 0.303 | [0.110; 0.834] |
| Any Tocilizumab use (yes vs no) for Treatment: Vilo | 0.339 | [0.136; 0.845] |
| Any Tocilizumab use (yes vs no) for Treatment: Placebo | 0.839 | [0.479; 1.468] |

*Wald-type confidence intervals; HR = Hazard Ratio; FAS = Full analysis set; SOC = Standard of care; Vilo = Vilobelimab C) Effect of Combined Treatment of Vilobelimab and Tocilizumab on Patient Survival In addition to the statistical analysis using Cox proportional hazard model the single and combined treatment of vilobelimab and tocilizumab was also analyzed with the Kaplan-Meier method. This is a non-parametric method used to estimate the survival probability from observed survival times and is typically plotted as Kaplan-Meier survival graphs.

The effect size of combined treatment of vilobelimab and tocilizumab (any usage) on all-cause mortality is dramatically increased as can be seen in FIG. 2. Treatment of vilobelimab combined with any usage of tocilizumab (line 1) shows only a slight increase of the probability of mortality within 60 days. In comparison, the group receiving placebo without any use of Tocilizumab (line 4) had a much higher mortality rate. The mortality rate in the groups receiving vilobelimab and standard of care (SOC) without tocilizumab (line 2) showed only a slight improvement. Patients treated with tocilizumab and SOC (line 3) showed an even lower improvement of survival rates. A virtually identical outcome was observed with baseline use of Tocilizumab (see FIG. 3).

The benefit of combined vilobelimab and tocilizumab treatment is even more pronounced within the first 22 days of treatment with hardly any fatalities in this treatment group. In contrast in the other treatment groups the majority of fatalities occurred in this time of treatment.

In summary, the combined treatment of vilobelimab and tocilizumab (baseline use and any use) resulted in a dramatic increase of survival probability as compared to the treatment with only one of the compounds or placebo. Of note the effect on survival rate of the combined treatment is much higher than the sum of the individual effects of vilobelimab and tocilizumab alone, indicating a synergistic effect of the combined treatment instead of a mere additive effect.

SEQUENCE LISTING

```
Sequence total quantity: 55
SEQ ID NO: 1            moltype = AA  length = 74
FEATURE                 Location/Qualifiers
source                  1..74
                        mol_type = protein
                        organism = Homo sapiens
SEQUENCE: 1
TLQKKIEEIA AKYKHSVVKK CCYDGACVNN DETCEQRAAR ISLGPRCIKA FTECCVVASQ  60
LRANISHKDM QLGR                                                   74

SEQ ID NO: 2            moltype = AA  length = 9
FEATURE                 Location/Qualifiers
source                  1..9
                        mol_type = protein
                        organism = Homo sapiens
SEQUENCE: 2
NDETCEQRA                                                         9

SEQ ID NO: 3            moltype = AA  length = 7
FEATURE                 Location/Qualifiers
source                  1..7
                        mol_type = protein
                        organism = Homo sapiens
SEQUENCE: 3
SHKDMQL                                                           7

SEQ ID NO: 4            moltype = AA  length = 7
FEATURE                 Location/Qualifiers
```

```
source                   1..7
                         mol_type = protein
                         organism = Homo sapiens
SEQUENCE: 4
DETCEQR                                                                  7

SEQ ID NO: 5             moltype = AA  length = 5
FEATURE                  Location/Qualifiers
source                   1..5
                         mol_type = protein
                         organism = Homo sapiens
SEQUENCE: 5
HKDMQ                                                                    5

SEQ ID NO: 6             moltype = AA  length = 10
FEATURE                  Location/Qualifiers
source                   1..10
                         mol_type = protein
                         organism = synthetic construct
SEQUENCE: 6
CQQSNEDPYT                                                              10

SEQ ID NO: 7             moltype = AA  length = 10
FEATURE                  Location/Qualifiers
source                   1..10
                         mol_type = protein
                         organism = synthetic construct
SEQUENCE: 7
CQQNNEDPLT                                                              10

SEQ ID NO: 8             moltype = AA  length = 13
FEATURE                  Location/Qualifiers
source                   1..13
                         mol_type = protein
                         organism = synthetic construct
SEQUENCE: 8
WYQQKPGQPP KLL                                                          13

SEQ ID NO: 9             moltype = AA  length = 12
FEATURE                  Location/Qualifiers
source                   1..12
                         mol_type = protein
                         organism = synthetic construct
SEQUENCE: 9
IDPSDSESRL DQ                                                           12

SEQ ID NO: 10            moltype = AA  length = 12
FEATURE                  Location/Qualifiers
source                   1..12
                         mol_type = protein
                         organism = synthetic construct
SEQUENCE: 10
ILPGSGSTNY NE                                                           12

SEQ ID NO: 11            moltype = AA  length = 7
FEATURE                  Location/Qualifiers
source                   1..7
                         mol_type = protein
                         organism = synthetic construct
SEQUENCE: 11
IYAASNL                                                                  7

SEQ ID NO: 12            moltype = AA  length = 7
FEATURE                  Location/Qualifiers
source                   1..7
                         mol_type = protein
                         organism = synthetic construct
SEQUENCE: 12
IYAASNL                                                                  7

SEQ ID NO: 13            moltype = AA  length = 14
FEATURE                  Location/Qualifiers
source                   1..14
                         mol_type = protein
                         organism = synthetic construct
SEQUENCE: 13
CKASGYSFTT FWMD                                                         14

SEQ ID NO: 14            moltype = AA  length = 14
```

```
FEATURE                 Location/Qualifiers
source                  1..14
                        mol_type = protein
                        organism = synthetic construct
SEQUENCE: 14
CKATGNTFSG YWIE                                                      14

SEQ ID NO: 15           moltype = AA  length = 16
FEATURE                 Location/Qualifiers
source                  1..16
                        mol_type = protein
                        organism = synthetic construct
SEQUENCE: 15
CKASQSVDYD GDSYMK                                                    16

SEQ ID NO: 16           moltype = AA  length = 16
FEATURE                 Location/Qualifiers
source                  1..16
                        mol_type = protein
                        organism = synthetic construct
SEQUENCE: 16
CKASQSVDYD GDSYMN                                                    16

SEQ ID NO: 17           moltype = AA  length = 13
FEATURE                 Location/Qualifiers
source                  1..13
                        mol_type = protein
                        organism = synthetic construct
SEQUENCE: 17
CARGNDGYYG FAY                                                       13

SEQ ID NO: 18           moltype = AA  length = 15
FEATURE                 Location/Qualifiers
source                  1..15
                        mol_type = protein
                        organism = synthetic construct
SEQUENCE: 18
CTRRGLYDGS SYFAY                                                     15

SEQ ID NO: 19           moltype = AA  length = 22
FEATURE                 Location/Qualifiers
source                  1..22
                        mol_type = protein
                        organism = synthetic construct
SEQUENCE: 19
DIVLTQSPAS LAVSLGQRAT IS                                             22

SEQ ID NO: 20           moltype = AA  length = 33
FEATURE                 Location/Qualifiers
source                  1..33
                        mol_type = protein
                        organism = synthetic construct
SEQUENCE: 20
QSGIPARFSG SGSGTDFTLN IHPVEEEDAA TYY                                 33

SEQ ID NO: 21           moltype = AA  length = 10
FEATURE                 Location/Qualifiers
source                  1..10
                        mol_type = protein
                        organism = synthetic construct
SEQUENCE: 21
FGGGTKLEIK                                                           10

SEQ ID NO: 22           moltype = AA  length = 111
FEATURE                 Location/Qualifiers
source                  1..111
                        mol_type = protein
                        organism = synthetic construct
SEQUENCE: 22
DIVLTQSPAS LAVSLGQRAT ISCKASQSVD YDGDSYMKWY QQKPGQPPKL LIYAASNLQS    60
GIPARFSGSG SGTDFTLNIH PVEEEDAATY YCQQSNEDPY TFGGGTKLEI K            111

SEQ ID NO: 23           moltype = AA  length = 21
FEATURE                 Location/Qualifiers
source                  1..21
                        mol_type = protein
                        organism = synthetic construct
SEQUENCE: 23
QVQLQQSGPQ LVRPGTSVKI S                                              21
```

```
SEQ ID NO: 24           moltype = AA  length = 15
FEATURE                 Location/Qualifiers
source                  1..15
                        mol_type = protein
                        organism = synthetic construct
SEQUENCE: 24
WVKQRPGQGL EWIGR                                                       15

SEQ ID NO: 25           moltype = AA  length = 33
FEATURE                 Location/Qualifiers
source                  1..33
                        mol_type = protein
                        organism = synthetic construct
SEQUENCE: 25
RFKDRATLTV DKSSSTVYMQ LSSPTSEDSA VYY                                   33

SEQ ID NO: 26           moltype = AA  length = 12
FEATURE                 Location/Qualifiers
source                  1..12
                        mol_type = protein
                        organism = synthetic construct
SEQUENCE: 26
WGQGTLVTVS SA                                                          12

SEQ ID NO: 27           moltype = AA  length = 120
FEATURE                 Location/Qualifiers
source                  1..120
                        mol_type = protein
                        organism = synthetic construct
SEQUENCE: 27
QVQLQQSGPQ LVRPGTSVKI SCKASGYSFT TFWMDWVKQR PGQGLEWIGR IDPSDSESRL       60
DQRFKDRATL TVDKSSSTVY MQLSSPTSED SAVYYCARGN DGYYGFAYWG QGTLVTVSSA      120

SEQ ID NO: 28           moltype = AA  length = 22
FEATURE                 Location/Qualifiers
source                  1..22
                        mol_type = protein
                        organism = synthetic construct
SEQUENCE: 28
DIVLTQSPAS LAVSLGQRAT IS                                               22

SEQ ID NO: 29           moltype = AA  length = 33
FEATURE                 Location/Qualifiers
source                  1..33
                        mol_type = protein
                        organism = synthetic construct
SEQUENCE: 29
GSGIPARFSG SGSGTDFTLN IHPVEEEVAA TYY                                   33

SEQ ID NO: 30           moltype = AA  length = 10
FEATURE                 Location/Qualifiers
source                  1..10
                        mol_type = protein
                        organism = synthetic construct
SEQUENCE: 30
FGAGTLLELK                                                             10

SEQ ID NO: 31           moltype = AA  length = 111
FEATURE                 Location/Qualifiers
source                  1..111
                        mol_type = protein
                        organism = synthetic construct
SEQUENCE: 31
DIVLTQSPAS LAVSLGQRAT ISCKASQSVD YDGDSYMNWY QQKPGQPPKL LIYAASNLGS       60
GIPARFSGSG SGTDFTLNIH PVEEEVAATY YCQQNNEDPL TFGAGTLLEL K               111

SEQ ID NO: 32           moltype = AA  length = 20
FEATURE                 Location/Qualifiers
source                  1..20
                        mol_type = protein
                        organism = synthetic construct
SEQUENCE: 32
VQLLESGAEL MKPGASVKIS                                                  20

SEQ ID NO: 33           moltype = AA  length = 15
FEATURE                 Location/Qualifiers
source                  1..15
                        mol_type = protein
```

```
                              organism = synthetic construct
SEQUENCE: 33
WVKQRPGHGL EWIGE                                                           15

SEQ ID NO: 34           moltype = AA  length = 33
FEATURE                 Location/Qualifiers
source                  1..33
                        mol_type = protein
                        organism = synthetic construct
SEQUENCE: 34
KFKGKATLTA DTSSNTAYMQ LSSLTSEDSA VYY                                        33

SEQ ID NO: 35           moltype = AA  length = 11
FEATURE                 Location/Qualifiers
source                  1..11
                        mol_type = protein
                        organism = synthetic construct
SEQUENCE: 35
WGQGTLVTVS A                                                               11

SEQ ID NO: 36           moltype = AA  length = 120
FEATURE                 Location/Qualifiers
source                  1..120
                        mol_type = protein
                        organism = synthetic construct
SEQUENCE: 36
VQLLESGAEL MKPGASVKIS CKATGNTFSG YWIEWVKQRP GHGLEWIGEI LPGSGSTNYN           60
EKFKGKATLT ADTSSNTAYM QLSSLTSEDS AVYYCTRRGL YDGSSYFAYW GQGTLVTVSA           120

SEQ ID NO: 37           moltype = AA  length = 22
FEATURE                 Location/Qualifiers
source                  1..22
                        mol_type = protein
                        organism = synthetic construct
SEQUENCE: 37
DIQMTQSPSS LSASVGDRVT IT                                                   22

SEQ ID NO: 38           moltype = AA  length = 16
FEATURE                 Location/Qualifiers
source                  1..16
                        mol_type = protein
                        organism = synthetic construct
SEQUENCE: 38
CKASQSVDYD GDSYMK                                                          16

SEQ ID NO: 39           moltype = AA  length = 13
FEATURE                 Location/Qualifiers
source                  1..13
                        mol_type = protein
                        organism = synthetic construct
SEQUENCE: 39
WYQQKPGKAP KLL                                                             13

SEQ ID NO: 40           moltype = AA  length = 7
FEATURE                 Location/Qualifiers
source                  1..7
                        mol_type = protein
                        organism = synthetic construct
SEQUENCE: 40
IYAASNL                                                                    7

SEQ ID NO: 41           moltype = AA  length = 33
FEATURE                 Location/Qualifiers
source                  1..33
                        mol_type = protein
                        organism = synthetic construct
SEQUENCE: 41
QSGVPSRFSG SGSGTDFTLT ISSLQPEDFA TYY                                        33

SEQ ID NO: 42           moltype = AA  length = 10
FEATURE                 Location/Qualifiers
source                  1..10
                        mol_type = protein
                        organism = synthetic construct
SEQUENCE: 42
CQQSNEDPYT                                                                 10

SEQ ID NO: 43           moltype = AA  length = 10
FEATURE                 Location/Qualifiers
```

| | |
|---|---|
| source | 1..10<br>mol_type = protein<br>organism = synthetic construct |

SEQUENCE: 43
FGQGTKLEIK                                                               10

| | |
|---|---|
| SEQ ID NO: 44<br>FEATURE<br>source | moltype = AA   length = 111<br>Location/Qualifiers<br>1..111<br>mol_type = protein<br>organism = synthetic construct |

SEQUENCE: 44
DIQMTQSPSS LSASVGDRVT ITCKASQSVD YDGDSYMKWY QQKPGKAPKL LIYAASNLQS        60
GVPSRFSGSG SGTDFTLTIS SLQPEDFATY YCQQSNEDPY TFGQGTKLEI K                111

| | |
|---|---|
| SEQ ID NO: 45<br>FEATURE<br>source | moltype = AA   length = 21<br>Location/Qualifiers<br>1..21<br>mol_type = protein<br>organism = synthetic construct |

SEQUENCE: 45
QVQLVQSGAE VKKPGASVKV S                                                 21

| | |
|---|---|
| SEQ ID NO: 46<br>FEATURE<br>source | moltype = AA   length = 14<br>Location/Qualifiers<br>1..14<br>mol_type = protein<br>organism = synthetic construct |

SEQUENCE: 46
CKASGYSFTT FWMD                                                         14

| | |
|---|---|
| SEQ ID NO: 47<br>FEATURE<br>source | moltype = AA   length = 15<br>Location/Qualifiers<br>1..15<br>mol_type = protein<br>organism = synthetic construct |

SEQUENCE: 47
WVRQAPGQGL EWIGR                                                        15

| | |
|---|---|
| SEQ ID NO: 48<br>FEATURE<br>source | moltype = AA   length = 12<br>Location/Qualifiers<br>1..12<br>mol_type = protein<br>organism = synthetic construct |

SEQUENCE: 48
IDPSDSESRL DQ                                                           12

| | |
|---|---|
| SEQ ID NO: 49<br>FEATURE<br>source | moltype = AA   length = 33<br>Location/Qualifiers<br>1..33<br>mol_type = protein<br>organism = synthetic construct |

SEQUENCE: 49
RFKDRVTMTV DKSTSTVYME LSSLRSEDTA VYY                                    33

| | |
|---|---|
| SEQ ID NO: 50<br>FEATURE<br>source | moltype = AA   length = 13<br>Location/Qualifiers<br>1..13<br>mol_type = protein<br>organism = synthetic construct |

SEQUENCE: 50
CARGNDGYYG FAY                                                          13

| | |
|---|---|
| SEQ ID NO: 51<br>FEATURE<br>source | moltype = AA   length = 11<br>Location/Qualifiers<br>1..11<br>mol_type = protein<br>organism = synthetic construct |

SEQUENCE: 51
WGQGTLVTVS S                                                            11

| | |
|---|---|
| SEQ ID NO: 52<br>FEATURE<br>source | moltype = AA   length = 119<br>Location/Qualifiers<br>1..119<br>mol_type = protein<br>organism = synthetic construct |

SEQUENCE: 52
QVQLVQSGAE VKKPGASVKV SCKASGYSFT TFWMDWVRQA PGQGLEWIGR IDPSDSESRL        60
DQRFKDRVTM TVDKSTSTVY MELSSLRSED TAVYYCARGN DGYYGFAYWG QGTLVTVSS        119

```
SEQ ID NO: 53          moltype = AA  length = 13
FEATURE                Location/Qualifiers
source                 1..13
                       mol_type = protein
                       organism = synthetic construct
SEQUENCE: 53
VNNDETCEQR AAR                                                              13

SEQ ID NO: 54          moltype = AA  length = 6
FEATURE                Location/Qualifiers
source                 1..6
                       mol_type = protein
                       organism = synthetic construct
SEQUENCE: 54
ISHKDM                                                                       6

SEQ ID NO: 55          moltype = AA  length = 5
FEATURE                Location/Qualifiers
source                 1..5
                       mol_type = protein
                       organism = synthetic construct
SEQUENCE: 55
GGGGS                                                                        5
```

The invention claimed is:

1. A method of treating infectious pneumonia and/or infectious acute respiratory distress syndrome (ARDS) caused by SARS-CoV-2 infection, the method comprising:
   administering to a patient in need thereof an inhibitor of C5a activity
   (i) in combination with an inhibitor of IL-6 activity; and/or
   (ii) wherein the patient is or has been treated with an inhibitor of IL-6 activity; and
   wherein the inhibitor of C5a activity is vilobelimab and the inhibitor of IL-6 activity is tocilizumab.

2. The method of claim 1, wherein said administering comprises a regime comprising an induction phase followed by a maintenance phase, wherein the inhibitor of C5a activity is administered in the induction phase and the maintenance phase and the inhibitor of IL-6 activity is administered:
   (I) within 0-30 days prior to the induction phase,
   (II) during the induction phase, and/or
   (III) during the maintenance phase.

3. The method of claim 2, wherein:
   (i) the induction phase comprises or consists essentially of a period of 1 to 10 days, wherein 1-8 doses, each comprising 200-1600 mg of said inhibitor of C5a activity, are administered; and
   (ii) the maintenance phase comprises or consists essentially of a period of at least 2 weeks, wherein a dose, comprising 200-1600 mg of said inhibitor of C5a activity, is administered every 1-4 weeks.

4. The method of claim 2, wherein:
   (i) 1 or 2 doses of the inhibitor of IL-6 activity is administered within 0 to 14 days prior and/or after the start of the induction phase; and/or
   (ii) the inhibitor of IL-6 activity is administered at a weight dependent dose of 8 mg/kg for patients at or above 30 kg weight or 12 mg/kg for patients of less than 30 kg weight.

* * * * *